United States Patent
Moulik

(10) Patent No.: US 9,232,895 B2
(45) Date of Patent: Jan. 12, 2016

(54) METHOD AND SYSTEM FOR AUTOMATIC INTERPRETATION OF COMPUTER TOMOGRAPHY SCAN DATA

(71) Applicant: Supratik Kumar Moulik, Columbus, OH (US)

(72) Inventor: Supratik Kumar Moulik, Columbus, OH (US)

(*) Notice: Subject to any disclaimer, the term of this patent is extended or adjusted under 35 U.S.C. 154(b) by 100 days.

(21) Appl. No.: 14/011,947

(22) Filed: Aug. 28, 2013

(65) Prior Publication Data

US 2013/0343630 A1   Dec. 26, 2013

Related U.S. Application Data

(63) Continuation of application No. 12/615,418, filed on Nov. 10, 2009, now Pat. No. 8,553,952.

(60) Provisional application No. 61/118,603, filed on Nov. 29, 2008.

(51) Int. Cl.
| | |
|---|---|
| *G06K 9/00* | (2006.01) |
| *A61B 5/00* | (2006.01) |
| *G06T 7/00* | (2006.01) |
| *A61B 6/00* | (2006.01) |

(52) U.S. Cl.
CPC ............. *A61B 5/0033* (2013.01); *G06K 9/00* (2013.01); *G06T 7/0012* (2013.01); *G06T 7/0081* (2013.01); *A61B 6/5211* (2013.01); *G06K 2209/051* (2013.01); *G06T 2207/10081* (2013.01); *G06T 2207/30004* (2013.01)

(58) Field of Classification Search
CPC combination set(s) only.
See application file for complete search history.

(56) References Cited

U.S. PATENT DOCUMENTS

| | | | |
|---|---|---|---|
| 2002/0114498 A1 | 8/2002 | Op De Beek et al. | |
| 2003/0176780 A1* | 9/2003 | Arnold | G06T 7/0012 600/407 |
| 2004/0131149 A1 | 7/2004 | Op De Beek et al. | |
| 2004/0223633 A1 | 11/2004 | Krishnan | |
| 2008/0192998 A1 | 8/2008 | Takeguchi et al. | |
| 2010/0278405 A1* | 11/2010 | Kakadiaris | G06F 19/3431 382/131 |

OTHER PUBLICATIONS

Webpage printed on Nov. 12, 2009, listing Product Literature available at the TeraRecon, Inc. website at http://www.terarecon.com/news/prod_literature.htm (2 pp.).

"Advanced Clinical Applications" brochure obtained from the TeraRecon, Inc. website at http://www.terarecon.com/downloads/products/0711_AQ_clinical_lowres.pdf (24 pp.).

* cited by examiner

*Primary Examiner* — Valerie Lubin
*Assistant Examiner* — Reginald R Reyes
(74) *Attorney, Agent, or Firm* — Chowdhury Law Group, P.C.

(57) ABSTRACT

Disclosed is a method for interpreting image data that represents variations in density of matter inside a subject. A data processing system receives image data from a scan of a subject. The data processing system automatically discerns one or more bones, one or more arteries, and one or more organs of the subject, based at least in part on the image data. The data processing system may also automatically identify one or more of the discerned bones, arteries, and organs. The data processing system may also automatically determine a branch point of one of the one or more arteries of the subject. The data processing system may also produce output that depicts one or more of the identified bones, one or more of the identified arteries, one or more of the identified organs, and/or or the outer or inner margin of the body wall. Other embodiments are described and claimed.

21 Claims, 14 Drawing Sheets

METHOD AND SYSTEM FOR AUTOMATIC INTERPRETATION OF COMPUTER TOMOGRAPHY SCAN DATA

CROSS REFERENCE TO RELATED APPLICATIONS

This application claims priority to U.S. patent application Ser. No. 12/615,418, incorporated herein by reference, which was filed on Nov. 10, 2009, by the same inventor of this application, and which claims priority to U.S. provisional patent application No. 61/118,603, incorporated herein by reference, which was filed on Nov. 29, 2008, by the same inventor of this application.

FIELD OF THE INVENTION

This invention relates generally to data processing. More particularly, this invention relates to the automatic interpretation of medical imaging data from computer tomography scanners, magnetic resonance imaging scanners, and the like.

BACKGROUND

Computer tomography (also known as computed tomography or CT) is a technology used to produce images of the interior of an object by irradiating the object, measuring the radiation scatter, and reconstructing images from this measured data to produce an interpretable set of images. CT is frequently employed in medicine to produce images of the inside of a human body to permit evaluation of a patient's medical condition. For instance, radiologists may detect anomalies such as tumors and aneurysms in CT images.

CT images show variations in density of the matter inside an object such as a human body utilizing grayscale images. For instance, a typical conventional CT image uses 12-bit grayscale, but other image encoding standards may be used in other embodiments. The shade of gray in which a particular area of a CT image is displayed corresponds to the radiodensity of that area in the imaged body, as measured in Hounsfield units (HU), where radiodensity is the relative transparency of a substance to x-rays. An area of a lung, for example, being mostly air, is rendered in a relatively dark shade of gray corresponding to an HU value approximating the HU value of air at standard temperature and pressure (i.e., −400 to −1024 HU). An area of an organ, in another example, being mostly of the same radiodensity as water, may be rendered in a relatively light shade of gray corresponding to an HU value that is close to the HU value of water at standard temperature and pressure (i.e., 0 HU). Similarly, muscle, which is denser than water, may be imaged in a lighter shade of gray corresponding to about +40 HU, and cortical bone, which is much denser than water, may be imaged at in an even lighter shade of gray corresponding to about +400 HU.

To be of use in evaluating the medical condition of a patient, a CT image must be interpreted by an expert in the field, generally a radiologist. The expert must bring to bear wide-ranging knowledge of the human anatomy and of the subtleties of CT imaging technology. Despite the advanced nature of the imaging technology and the computer technology used to produce CT images, the radiologist must typically devote significant and valuable time to the analysis and interpretation of an image to produce a correct evaluation of the imaged patient's condition. Radiologists are called upon to interpret an increasing number of images as the use of CT imaging increases.

SUMMARY

In one aspect, a method for automatically interpreting data from a CT scanner or similar device involves receiving the CT scan data at a data processing system. The CT scan data may have been collected by scanning a human subject, for instance. Automatic image recognition (AIR) software in the data processing system may then automatically recognize various anatomical structures represented by the scan data. Accordingly, the AIR software may also be referred to as automatic structure recognition (ASR) software. This software may recognize, for instance, one or more of the following structures: an outer margin of the body wall, an inner margin of the body wall, muscles, bone margins, particular bones, margins of blood vessels, particular blood vessels, margins of organs, particular organs, and variations from normal anatomy (e.g., aneurysms). The AIR software may then produce output that identifies the recognized structures. The output may be used by a person to evaluate the health of the subject.

Another aspect pertains to a machine-readable medium containing some or all of the instructions that constitute the AIR software. Another aspect pertains to a data processing system or computer to execute the AIR software. Some embodiments may involve hardware, software, or combinations of hardware and software for performing operations such as those described herein.

The foregoing is a summary and thus contains, by necessity, simplifications, generalizations, and omissions of detail. Numerous additional details for one or more embodiments are described in the text and drawings of the present disclosure.

DETAILED DESCRIPTION

Figure 1:
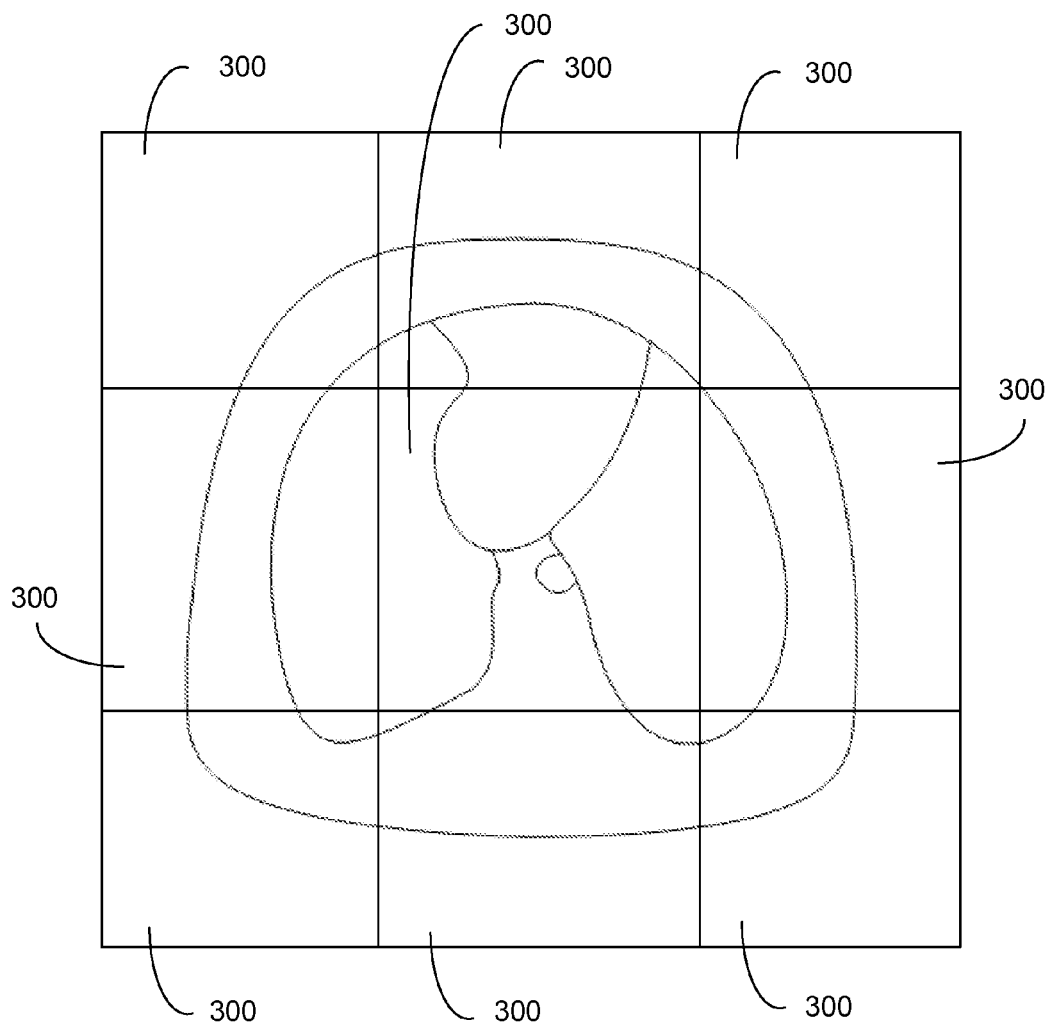
FIG. 1 is a line drawing that represents a slice of a CT scan divided into nine quadrants.

In the following detailed description, reference is made to the accompanying drawings, which form a part hereof. The illustrative embodiments described in the detailed description, drawings, and claims are not meant to be limiting. Other embodiments may be utilized, and other changes may be made, without substantially departing from the spirit or scope of the subject matter presented here.

Aspects of the present invention use computer hardware and software to automatically discern and identify anatomical structures in digital images of the interior of an animal subject. An example embodiment processes CT images of the human body, where those images comport with the digital imaging and communications in medicine (DICOM) standard, with attributes such as header information regarding the volume/slab thickness of the data.

Alternative embodiments may process three-dimensional (3D) image data from other types of scanners (e.g., magnetic resonance imaging (MRI) scanners). In addition, alternative embodiments may process digital images of non-human mammals or other animal subjects.

A basic goal of CT image interpretation is to identify correctly the anatomical structures in the image. One or more embodiments of the present invention provide for the automatic discernment of anatomical structures including but not limited to (a) the outer margins of the body (i.e., the outside surface of the body); (b) the inner margins of the body wall, inside of which are contained all of the abdominal and thoracic organs; (c) the margins of the visceral organs; (d) the margins of bones; (e) the margins of blood vessels; and (f) the branch points of blood vessels. Particular bones, organs, blood vessels, branch points, and other structures may also be automatically discerned and identified. For purposes of this disclosure, to "discern" that a structure is bone is to determine that the structure is made of bone. By contrast, to "identify" a bone is to determine which particular bone that structure is. For instance, an automated system may "discern" which parts of an image represent bone, and the system may "identify" a particular part of the image as the right twelfth rib. In addition, this disclosure uses the terms "discern" and "identify" in a like manner with regard to other types of structures, such as blood vessels. Embodiments may also provide for the automatic recognition and identification of normal anatomic variants and abnormalities such as aneurysms.

A key principle in image recognition in general and medical imaging specifically is the concept that adjacent structures are discernable due to interfaces. Specifically, the differential x-ray penetration through adjacent organs of varying density produces an interface which allows the two organs to be perceived as distinct. For example, if two different structures with similar density share a common border, those structures will be indistinguishable. The large differences in density that make medical images interpretable are provided primarily by body fat and injected intravenous contrast material (usually iodine based). A margin, which lies at the surface of a structure, is often the most easily identifiable feature of a structure because tissue densities typically change at the margins, and the CT image consequently shows changes in gray shading at the margins. By automatically discerning and identifying anatomical structures, the technology described herein may reduce or eliminate the time required for a radiologist to identify those structures, thereby freeing time for the radiologist to interpret anomalies and other aspects of a patient's condition.

Embodiments of the invention may use threading to allow optimal use of multicore computer system resources. Further, embodiments may use one or more graphical processing units (GPUs) to run some or all of the algorithms described herein. For instance, embodiments may use the NVIDIA® 280 GTX GPU or the NVIDIA® 8800 GTX GPU. For some embodiments, algorithms may be implemented using the Computer Unified Device Architecture (CUDA) or the Open Computing Language (OpenCL) compilers and development tools. Some embodiments may use an implementation of the Open Graphics Library (OpenGL) graphics specification to display graphical output. In addition, the cluster communication specification defined in the Message Passing Interface (MPI) standard may be used to distribute the workload across multiple computers with shared CPU and GPU capabilities. The control functions and some or all of the algorithms described herein may be written in the C/C++ programming language. In some embodiments, one or more neural networks may be used to perform some of the operations described herein.

Figure 10:
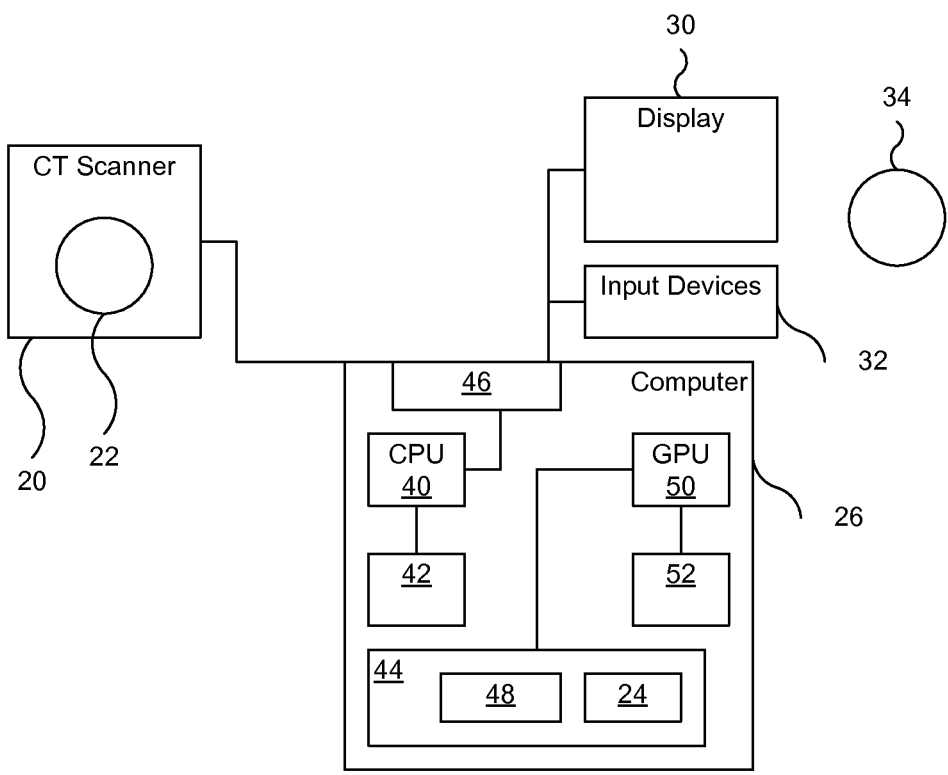
FIG. 10 is a schematic diagram depicting an example embodiment of a data processing system programmed to provide for automatic structure recognition.

FIG. 10 is a schematic diagram depicting an example embodiment of a computer or data processing system 26 programmed to provide for automatic recognition of anatomical structures in CT scan data. In the embodiment of FIG. 10, the computer includes one or more central processing units (CPUs) 40, and one or more graphics processing units (GPUs) 50. The CPU is coupled to system random access memory (RAM) 42, and the GPU is coupled to graphics RAM or graphics memory 52. One or more input/output (I/O) devices or ports 46 are also coupled to the CPU, as are one or more mass storage devices, such as a hard disk drive (HDD) 44, nonvolatile memory, etc.

Also depicted in FIG. 10 is a CT scanner 20, which scans a human subject 22, thereby generating CT scan data. This scan data is received from the CT scanner by the computer. The computer may then store some or all of the scan data 24 in the HDD, for instance.

The computer also contains software for automatically recognizing anatomical structures in CT scan data. For ease of reference, such software may be referred to as automatic image recognition (AIR) software or automatic structure recognition (ASR) software, as indicated above. In the embodiment of FIG. 10, the AIR software 48 is stored on HDD 44, and the computer loads some or all of AIR software into the RAM and/or the graphics memory, and executes the software on the CPU and/or the GPU, as described in greater detail below.

A user 34 may interact with the computer via one or more input devices 32 (e.g., a keyboard, a pointing device, etc.) and one or more output devices, such as a monitor 30 and a printer. In one embodiment, the computer automatically detects the blood vessels of the vascular system simultaneously or substantially simultaneously with determining other structures, such as the body wall and/or the bones. In other embodiments, different types of structures may be detected in sequence. Output from these functions may help a user to interpret CT images.

Figure 11:
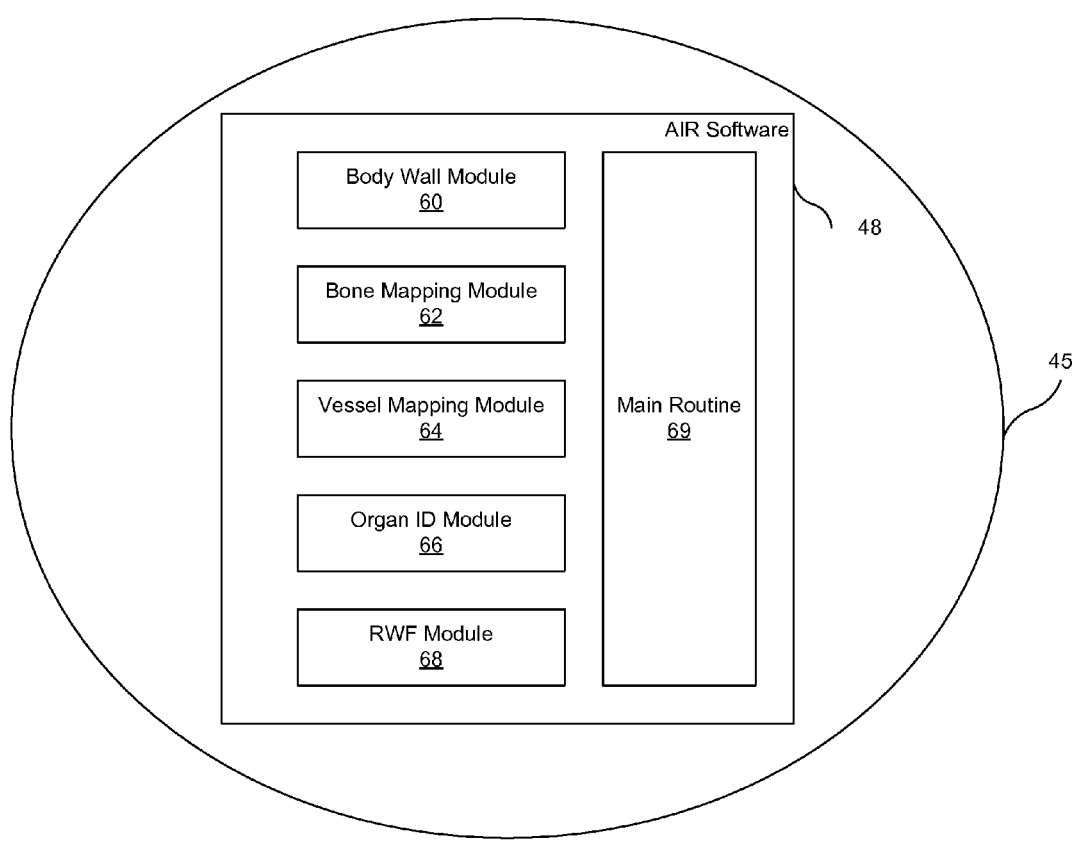
FIG. 11 is a schematic diagram of an example embodiment of an article of manufacture for converting a general purpose computer into a special purpose computer capable of recognizing anatomical structures from CT scan data.

FIG. 11 is a schematic diagram of an example embodiment of an article of manufacture for converting a general purpose computer into a special purpose computer capable of recognizing anatomical structures from scan data. In one embodiment, the AIR software is produced on an optical disk 45, a flash memory device, or any other suitable non-volatile data storage medium. The computer of FIG. 1 may copy some or all of the AIR software from the non-volatile data storage medium, install the AIR software, and then execute the AIR software.

As shown in FIG. 11, in one embodiment, the AIR software includes different components for performing different kinds of tasks. For instance, the AIR software may include a main routine 69 to manage the overall process, a body wall module 60 for discerning and identifying inner and outer body wall margins in an image, a bone mapping module 62 for discerning and identifying bones in the image, a vessel mapping module 64 for discerning and identifying blood vessels in the image, an organ identification module 66 for discerning and identifying particular organs, and a reverse wire framing module 68 for discerning and identifying margins of anatomical structures.

Figure 12:
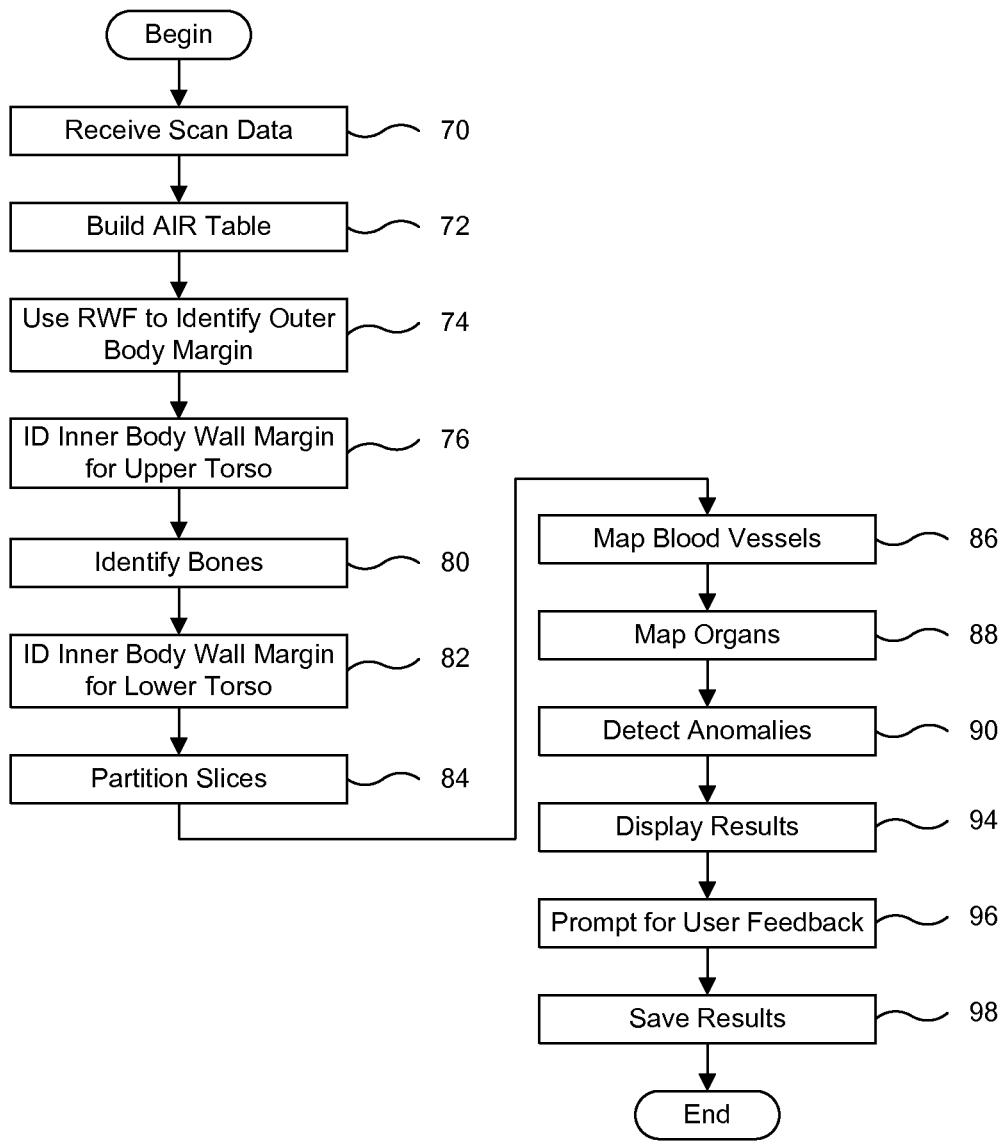
FIG. 12 is a flowchart of an example embodiment of a process for automatically recognizing anatomical structures from CT scan data.

FIG. 12 is a flowchart of an example embodiment of a process for automatically discerning and identifying anatomical structures from scan data. As depicted at block 70, this process may begin with the computer receiving or accepting CT scan data as input. The CT scan data may also be referred to as the CT image data. As received, the CT image data includes multiple slices, with each slice including data that defines or represents multiple voxels. Voxels are similar to pixels (picture elements), but pixels encode two-dimensional (2D) data, while voxels encode 3D data. Thus, voxels can represent distinct volume elements within a three-dimensional measurement of the subject, with the rows and columns corresponding to X and Y axes, and the different slices corresponding to different positions along a Z axis.

Furthermore, each individual slice in the CT image data may represent an averaging together of the data in N scans of the body. For example, a CT scanner could scan in 1400 slices, each about 0.3 millimeters (mm) apart, and then that raw data could be converted into CT image data with only 700 slices. Each slice in the CT image data could have a thickness of about 0.6 mm, and the content of each slice could represent an averaging of two consecutive raw slices.

For example, in one embodiment, the CT image data that is received as input includes data for 700 slices, with a slice thickness of 0.625 mm, and each slice contains 262,144 voxels, arranged in 512 rows and 512 columns, with a pixel dimension of approximately 0.7-0.9 mm. Greater or lesser voxel counts or resolutions may be used in other embodiments. Other embodiments may also use greater or lesser numbers of slices for the raw scan data, for the CT image data, or for both.

In the CT image data, each voxel has an associated numerical value corresponding to its HU value. As explained above, the HU value of a voxel represents the radiodensity of the matter in the CT image at the location of the voxel. The CT scan data may also be referred to as CT image data. The data processing system may store the accepted CT image data as a data array, with each element of the data array holding the data for one voxel of the CT image.

In addition, according to at least one embodiment, the AIR software computes a numerical value known as a gradient value for each voxel, and stores that value in association with that voxel value. The gradient value is computed by taking the average of the density gradients between the voxel and its six neighboring voxels—i.e., the four voxels directly adjacent to it in the slice, and the two voxels directly adjacent to it in the two adjacent slices. Thus, the gradient value corresponds to the relative value of the voxel, compared to its neighboring voxels. (With regard to such comparison, the compared voxel may be referred to as a first voxel, and the neighboring voxel may be referred to as a second voxel. For brevity, the terminology "compare a voxel" may be used rather than "compare a radiodensity value of a voxel," or the like.) Accordingly, large gradient values signify large differences in density between adjacent voxels. However, the AIR software may set a minimum threshold for what constitutes a significant gradient. In addition, the AIR software may exclude isolated gradient points as likely representing random noise. For example, at a true interface, each point will have neighbors which have similar gradient values. Conversely, if a point does not have any adjacent points with similar gradient values, it is likely to be related to random noise (referred to as quantum mottle).

As described in greater detail below, the AIR software may also (a) discern specific anatomical structures within the CT image, (b) assign different numbers to the identified anatomical structures, and (c) assign the pertinent anatomical structure number to each voxel belonging to an identified anatomical structure. For example, the AIR software may assign the identification number X to the left iliac crest of the pelvic bone, and if the AIR software determines that the matter imaged by particular voxels is part of the left iliac crest of the pelvic bone, and the AIR software may then assign the number X to each of those voxels.

Thus, the AIR software creates and populates one or more data structures to facilitate the automatic discernment and identification of anatomical structures in CT scan data. For instance, such a data structure may include a three dimensional array of elements, with one element for each voxel, and with each element capable of storing three types of values: one for the HU value of the voxel, one for the corresponding gradient value, and one for the corresponding anatomical structure identity value. Other types of data structures may be used in other embodiments. For ease of reference, this disclosure refers to the data structure(s) that holds these types of data elements as an AIR table.

Block 72 represents operations such as computing the gradient values for each voxel in the scan data, and populating the AIR table with the gradient values and the HU values. The AIR software may subsequently use the AIR table to discern the anatomical structures reflected in the CT image data accepted as input, and may update the AIR table with data identifying the anatomical structures so discerned.

In particular, as shown at block 74, after populating the AIR table with the HU and gradient values, the AIR software may analyze each slice to identify the outer margin or wall of the subject's body. In one embodiment, the AIR software uses the reverse wire framing module to determine which voxels in each slice correspond to the outer body margin.

1. Reverse Wire Framing

Regarding the "wire frame" terminology, conventional wire framing is a method used in computer graphics, in which lines are used to form the edges and surfaces of objects. The lines may then be replaced with other shapes or textures to provide a more realistic image.

By contrast, reverse wire framing (RWF) starts with an image of a real object, and then lines are used to discern different structures within that image. For instance, reverse wire framing may be used for contiguous edge detection. As described in greater detail below, the AIR software may take raw CT image data as input, and then the AIR software may, in effect, superimpose points, lines, closed loops (e.g., circles), and other shapes over the images, in a process for detecting margins of structures. For example, the AIR software may create a line with respect to a particular position in an image slice, and the AIR software may then move, extend, and otherwise modify that line until certain boundary conditions are met. The lines and other virtual objects that the AIR software uses for RWF may also be referred to as virtual lines, virtual loops, etc. Also, the term "line" is not limited to straight lines, but also covers arcs, curved lines, bent lines, etc.

The boundary conditions may also be referred to as "RWF boundary parameters," and they may include both tethering conditions (for fixing the position of points on the RWF line along a detected margin), and predefined constraints (for limiting the movement or fixing the position of points on the RWF line that have not been tethered). Also, the AIR software may use different boundary conditions for different purposes.

When a boundary condition is met, the RWF module stops or anchors the part of the line satisfying the boundary condition, while the other parts of the line are left free to move. In particular, parts of an RWF line may be fixed or moveable, and fixed parts may either be tethered (due to a tethering condition) or constrained (due to a predefined constraint). Accordingly, a part that is fixed due to a predefined constraint may be referred to as "untethered." The amount of movement to be allowed for a moveable part is constrained to a certain degree, depending on the predefined constraint associated with the current operation. The AIR software may use loose constraints for some purposes, and tighter constraints for other purposes. For example, a loose constraint may allow a moveable point on the line to move up to three millimeters away from an adjacent fixed point, while the tight constraint may not allow the moveable point to move more than one millimeter away from an adjacent fixed point. In another embodiment, the square root of two could be a tight constraint and two times the square root of 2 could be a loose constraint. In other embodiments, tight constraints might range from 0.5 mm to 1.5 mm, while loose constraints might range from 1.5 mm to 3 mm. Other embodiments may use different distances to constrain adjacent points on the line.

In addition, adjacent points of the wire frame do not necessarily need to have a fixed relationship in Cartesian coordinates. In the field of informatics, the use of fixed Cartesian coordinate distances is referred to as "snaking" Snaking is a subset of a more general class of processes for handling positions. In one embodiment, the AIR software does not use snaking algorithms. For example, the discussions below regarding evaluation of vessel lumens and organs makes reference to the condition that adjacent points have radial relations (e.g., spherical polar coordinates for the kidney and cylindrical coordinates for the vessel lumen) which are constrained, rather than Cartesian relations.

2. Discerning the Outer Body Wall

Referring again to block 74, as indicated above, the AIR software may analyze each slice to identify the outer wall of the subject's body. For instance, to detect the outer margin of the body, the AIR software may use a tethering condition that depends on the HU values for a series of points connected to a given point. In particular, when evaluating point P(x, y, z), the AIR software may analyze a predetermined number N of adjacent points radially inward from point P, along with a predetermined number M of adjacent points radially outward from point P. If the first adjacent point radially inward has a HU value in the range of epidermal tissue, then the program continues to evaluate radially inward to ensure that there are at least N contiguous points which have HU values within a range compatible with fat or other body wall tissues. When evaluating radially outward, there must be at least M points which have HU values compatible with air. Once all of these conditions are met, the AIR software may tether the point P as an outer margin of the body. In one embodiment, the body wall module uses a relatively loose constraint (e.g., 2 mm) to detect the outer body margin.

After discerning the outer body wall margin, the AIR software may update the AIR table to identify the relevant voxels accordingly.

The RWF module may use different shapes and methodologies for determining the tether points for the RWF. For instance, after the AIR software has identified an approximate center point of the body, the RWF module may shrink a large circle (or other curved, closed shape) radially inward while searching for the tethering condition for each point on the circle. This shrinking may be performed in a stepwise fashion, in that all points of the line move one unit distance in the desired direction, and once the tethering conditions for each point is evaluated at this new position, the process of move and evaluate is repeated. Alternatively, the RWF module may position a line at the x=0 position and then move the line to the right (increasing x) using the same kind of stepwise evaluation for tethering conditions. The stepwise progression of some points in the line may be interrupted once those points contact the body wall. The non-tethered points may continue with the stepwise progression until those points contact the body wall, thus wrapping around one side of the body wall. This process can be repeated for the other sides of the body (e.g., the top and side margins). Also, to cope with the complexity added by the scanner table along the inferior margin of the body wall, the RWF module may seek the same body-wall-margin interface starting from the middle and moving outward. The RWF module may use the same or similar techniques for building RWFs for other parts of the body. In addition, in alternative embodiments, other types of shapes may be used for the virtual wire frame line/loop, along with other possible starting positions and movement methodologies for locating boundary conditions.

3. Discerning the Inner Body Wall for the Upper Torso

The body wall of the torso or trunk includes a portion of the axial skeleton and the pelvis, plus muscle, fat, and skin tissue. After identifying the outer margin of the body wall, the body wall module may identify the inner margin of the body wall for the upper torso. In the embodiment of FIG. 12, the AIR software first discerns the inner body wall margin for the upper torso, as shown at block 76. As described in greater detail below, the AIR software then discerns the bones, as depicted at block 80, and then the inner body wall margin for the lower torso as depicted at block 82. Once the inner body wall margin is determined, the AIR software may more easily find anatomical structures (e.g., the visceral organs) which reside within the inner margin.

Lung tissue, being mostly air, provides a large radiodensity gradient compared with the radiodensity of every other kind of tissue. Lung tissue abuts the inner margin of the body wall at every point in an image that includes both the lung tissue and the body wall, except (a) where the heart abuts the inner margin in the anterior (forward) area and (b) where the posterior mediastinum abuts the inner margin in the posterior (rearward) area.

As described in greater detail below, the body wall module may use data regarding bones discerned within the chest to help with determining the inner margins of the body wall. For instance, the body wall module may use points along the spine and the ribs as potential locations for the inner body wall margin. The body wall module may use this large number of potential inner wall points to achieve a best fit with an anatomical model of the upper torso. In addition, the body wall module may use every point that represents a lung/tissue interface as a potential inner wall margin. The body wall module may then determine a combination of factors that yields the highest number of positive matches between an anatomical model of the spine and ribs and the potential inner wall points in the CT image. The body wall module may thus use a combination of lung interface locations and bone locations for the inner margins of the body wall in the chest area.

The body wall module may start the process of detecting the inner body wall of the upper torso by selecting a particular slice expected to contain a substantial amount of lung. For example, the CT scan data may contain 700 slices, each representing a cross section of 0.625 mm, with the scan starting at the bottom of the lungs and progressing through the proximal femurs. The chest portion of such a scan would typically involve the first 16-32 images of the set. The AIR software may start the process of finding the inner body margin at slice 0. In one embodiment, the AIR software makes no initial assumption as to whether or not images past slice 16 represent chest portions. Instead, RWF algorithms later in the process check to see if the lung/chest wall interface is present and where the transition from lung to abdomen occurs in the various quadrants of the scan.

Figure 2:
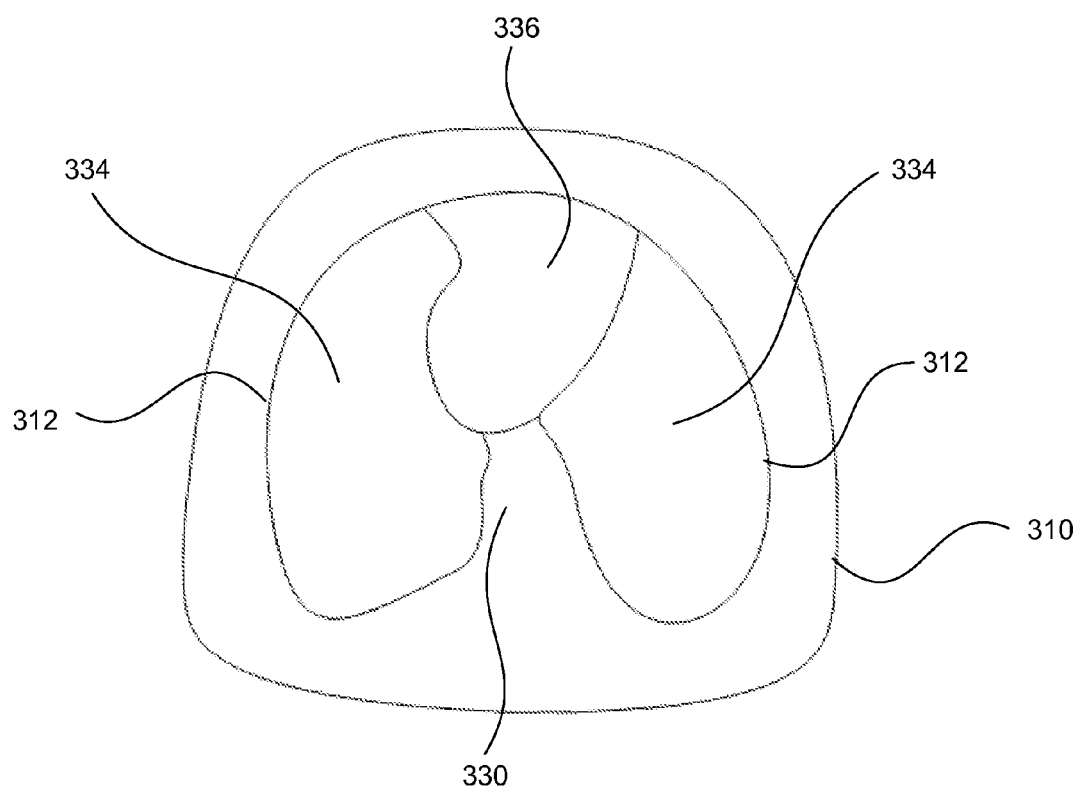
FIG. 2 is line drawing that represents a single slice of a CT image, including an outer margin of a body wall and an inner margin of the body wall.

FIG. 2 illustrates a simplified version of single slice of a CT image including the outer margin 310 of the body wall and the inner margin 312. As shown in FIG. 2, the lungs 334, the heart 336, and the posterior mediastinum 330 lie within the outer margin 310 of the body wall and abut the inner margin 312 of the body wall.

The body wall module may start by analyzing slice 0 to detect the inner body wall margin. In the embodiment of FIG. 12, the body wall module uses the RWF module to discern the inner margin of the body wall in the selected CT image slice. For example, within the chest portion of the scan (e.g., for the initial approximately 15-30 images), the initial step may be to compare the current scan with an anatomical model of the chest wall. (As described in greater detail below, such an anatomical model may have been extracted from a sample scan initially, and then progressively modified by incorporating data from subsequent scans.) The model may consist of a 512×512×N map of floating point numbers which give the probability that the corresponding point is part of the inner margin of the body wall. The model is taken through many different modifications or deformations (e.g., several million deformations). These modifications include scaling in the x-y plane, rotation in 3D, and deformation in one or more off axes (e.g., along the x=y axis). Deformations may include scaling along the z axis and other deformations. For example, two off axes may be defined, one at 45 degrees and the other at −45 degrees, with respect to the major axis. Normally, the shape or eccentricity of an ellipse is determined by the ratio of major: minor axis. However, for the inner margin of the chest wall, the shape can be anywhere from circular to a more square like configuration. The AIR software may account for larger variations in contour by scaling/deforming the ellipse along four or more axes (e.g., major, minor, and two off-axes). For purposes of this disclosure, the term "applying an anatomical model" is used to refer to operations for comparing features or structures from the subject with features or structures from one or more predefined anatomical models, possibly including modification or deformation of those models.

The AIR software may determine that a best fit between the current scan and a particular modification of the model has been found when the scan and that model have the maximal number of matching points which have soft tissue density (e.g., HU values of 20-50) radially outward and air density (e.g., HU values of <−200) radially inward. The AIR software may then apply that modified model to the current slice as a preliminary determination, by tethering the RWF line in areas determined to be lung/body wall interface. Thus, the primary method for identifying the inner margin of the body wall in the chest is to look for the lung/body wall interface (i.e., N points with soft tissue or fat density radially outward and M points with air density radially inward).

However, this lung/body wall interface does not exist along the posterior margin of the anterior chest wall, where the heart is juxtaposed with the chest wall. Therefore, in that area, the AIR software concludes that the inner margin has been passed and therefore tethering is required based on limits derived from the anatomical model. Similar techniques may be used where the body wall module expects the posterior mediastinum to abut the anterior portion of the posterior chest wall. The AIR software may use other techniques to detect the inner margin of the body wall in other regions. In one embodiment, approximately 24 different tethering conditions are used for detecting the inner margin of the body wall for different parts of the body.

The preliminary determination that tethers the RWF line for areas of the slice that contain a lung/body wall interface is then combined with the determinations that tether the RWF line for portions of the slice where the body wall abuts structures other than the lung (such as the heart or the posterior mediastinum), to produce a final determination of the inner wall margin for that slice. The AIR software may then use the same or similar techniques to discern the inner margin in the other slices of the upper torso containing lung tissue. In other words, the body wall module may repeat the above process for subsequent slices, until the AIR software reaches a slice that does not have N points with soft tissue of fat density radially outward and M points with air density radially inward. For example, in one embodiment, the body wall module typically processes 15-30 slices with the techniques described above. After finally determining the inner margin of the body wall for the upper torso, the AIR software may update the relevant voxels in the AIR table accordingly.

4. Discerning the Bones

After identifying the outer margin of the body wall and the inner margin of the body wall for the upper torso, the AIR software may use the bone mapping module to discern and identify the bones in the scan data, as shown at block 80 of FIG. 12. The control logic for finding the bones in the CT scan data may be referred to as a bone propagation algorithm. Furthermore, the bone propagation algorithm may be hardware accelerated. For instance, the AIR software may run the bone propagation algorithm on one or more GPUs. In one embodiment, the bone mapping module loads the entire CT image data set into the graphics memory, and then applies the bone propagation algorithm to that data.

There are two main types of bone tissue: cortical and medullary. Medullary tissue makes up the interior of most bones. As described in greater detail below, the bone mapping module may determine both types of bone tissue in CT scan images. For instance, the bone mapping module may use the bone propagation algorithm to discern cortical bone, and to compare the current scan with anatomical models of the various bones, to determine the inner margins and outer margins of cortical bone. The comparison with the anatomical model may involve the use of GPUs to perform numerous combinations of deformations, to find the optimal fit between the cortical bone of the model and the cortical bone of the scan. The bone mapping module may then (a) select candidate points on those margins, and (b) compare those points to one or more anatomical models of bone structure, to (c) identify particular bones.

In one embodiment, the bone propagation algorithm uses a predetermined radiodensity threshold to detect bones, while limiting the analysis to voxels within the body wall. The bone propagation algorithm may determine that all voxels within the area determined to be body wall with a HU value greater than or equal to this threshold represent cortical bone tissue. For instance, the bone mapping module may use a threshold value of 400 or a range of values from 400 to 1000, such that every voxel within the area determined to be body wall within this range is determined to be cortical bone.

The bone propagation algorithm only considers points within the body wall to be potential bone points since there can be areas of similar density inside the abdomen or chest due to dense calcifications. By contrast, if the program were to take any voxel within a certain radiodensity range and call it bone, whether that point was within the body wall or not, the program would be unable to distinguish between bone and calcification in vessel walls, for example. Consequently, a radiologist or specialized technologist would need to examine the results and manually remove extraneous calcifications before accurate 3D images could be rendered.

In addition to flagging voxels above the threshold as cortical bone, the bone mapping module may also determine that every voxel with sufficient physical and radiodensity continuity with the cortical bone voxels also represents cortical bone. For instance, the program may start with the first slice where the inner and outer margins of the body wall are easy to distinguish, since there air inside (lung) and outside. In that limited region of interest, the program first looks for voxels with very high density (>400 HU). It then checks voxels immediately adjacent to those voxels, and determines if they are within a broader range for cortical bone (e.g., HU=250-650). That comparison process is repeated N times with each iteration adding additional voxels or points. The bone mapping module may use this process to generate a preliminary RWF determination of the outer margins of all of the bones in the scan.

After finding all the voxels in the body wall that are cortical bone, the bone mapping module uses RWF techniques to connect the rib cage with the pelvis, to discern the iliac crest, and to locate the spine. This is accomplished by starting a RWF at the 12th ribs bilaterally (and draped over the spine). The RWF is moved posteriorly in three dimensions with the tethering condition of finding points that are predetermined to be cortical bone. The iliac crests are the most cephalad points in the bony pelvis when the spine is excluded. By discerning the spine at this stage, the AIR software is able to exclude the spine for subsequent lumen tracking work. The bone mapping module also uses the knowledge of the locations of the iliac crests and the spine to identify other points in the pelvis (e.g., the anterior and superior iliac crests, the right and left pubic symphysis, and the right and left femoral heads and shafts).

The bone mapping module then automatically lines up the anatomical models (for which the key point are predetermined) with the newly determined points on the current scan. This provides an initial estimate for the orientation of the bones of interest. Similar to the inner margin of the body wall, the program has a set of statistical maps corresponding to each of the major bone and bony structures that the program expects to encounter. Since cortical bone (which is heavily calcified and dense) has a relatively distinct HU value (which exceeds arterial contrast by a significant amount in a normal patient), the program tries to find a best fit between the anatomical model and the current scan. Once this is found, the model is applied to the scan.

For example, the anatomical model of the right femur is lined up so that the points identified as femoral head and femoral shaft on the current study line up with the corresponding points in the model. Similarly, with regard to identifying the pelvic bone, once the RWF module has discerned the margins of the pelvis, portions of the tethered RWF lines for those margins will coincide with various bony or cartilaginous features of the pelvis, such as the left and right iliac crests (the highest points of the pelvis); the left and right anterior superior iliac spines (the most anterior lateral points of the pelvis); the pubic symphysis (the most anterior and midline feature of the pelvis); and the coccyx (the most posterior, inferior and midline feature of the pelvis). The bone mapping module may automatically identify those features, and then attempt to map some or all of those points to corresponding points in anatomical models of various bones until a matching shape is found.

The bone mapping module may apply various deformations to the anatomical model, to fine tune this alignment until an optimal fit is found. For instance, the bone mapping module may confirm the margins of the pelvis in the CT image by applying multiple degrees of conformity to match discerned features from the image with features of models from the database. For example, in one embodiment, the bone mapping module uses multiple degrees of conformity to match discerned features from the image against features of model structures from the database. These degrees or vectors for deformation may include scale factors in height, width, and depth; translational factors in height, width, and depth; rotational factors, in terms of spherical coordinates, in zenith angle ($\theta$) and angle from an x-axis ($\phi$); and radial distance, which may be broken up into 3 components for scale. Applying deformations is important because of the complex morphology of most bones.

Also, even though the matching is performed on cortical bone, the medullary bone portion of the anatomical model is also deformed by the same parameter and applied to the scan image. In other words, the bone mapping module uses the deformation parameters which optimally match cortical bone and applies them to the model points which correspond to medullary bone. By default, the bone mapping module only treats voxels which are between the inner and outer margins of cortical bone as medullary bone.

In addition, since there are numerous individual bones with complex (though consistent) morphology, the AIR software may use anatomical models of bones to help detect the outer margin of each bone, or to finalize the determination of those outer margins. In one embodiment, after the bone mapping module has applied the anatomical models, the RWF algorithm attempts to find the cortical bone/fat interface as a tethering point. However, this process is bounded by the applied anatomical model, to prevent interference from adjacent bones and vessels which have similar density values.

The bone mapping module may determine that all voxels within the cortical margins or tables of each bone, including the medullary bone, represent bone tissue. This process of identifying bones and anatomic landmarks, fitting models, discerning and finalizing the outer margins, etc. may be utilized for all bones in the scan (including, for example, the bones of the pelvis, the spine, and the rib cage). The bone mapping module may update the AIR table accordingly, adding identifiers for particular bones and for parts of bones to the corresponding table elements.

Thus, the bone mapping module may accurately discern and identify all bone tissue in a CT image, and not just cortical bone. Consequently, the AIR software may perform highly accurate virtual bone extraction (e.g., to facilitate image analysis for other types of structures), rather than only disregarding cortical bone.

In another embodiment, the user interacts with the AIR software and provides user input to identify one or more anatomical structures or features. For instance, the user may identify the iliac crests and other points on the pelvis. The body wall module may then use that information to compare the subject pelvis against a database of anatomical models, to determine which bone is under review. Similar techniques may be used to identify the other bones in the image.

The AIR software may also output the results of the bone mapping in graphical form for visual review by the user. Furthermore, once the bones have been identified, the AIR software may use that information to help with other tasks, such as discerning the inner body wall margin. For example, in the area below the lungs, the body wall module may use the RWF module to tether a line segment to a bone structure, the pelvis, to help with determining the inner margin of the body wall, as described in greater detail below.

5. Discerning the Inner Body Wall for the Lower Torso

After the body wall module determines the inner margin of the body wall for the upper torso and the bone mapping module determines the bones, the body wall module determines the inner margin of the body wall for the lower torso, as shown at block 82. The lower torso or abdomen includes the area from the last slice containing lung tissue to the end of the scan, which typically includes the proximal femurs. In this area of the body, there are generally no strong differences in radiodensity to clearly distinguishing between organs and the inner margin of the body wall. However, the spinal bones are part of the body wall and are easily determined by methods described above with regard to bone mapping.

To continue determination of the inner margin of the body wall, the body wall module uses the RWF module to tether a RWF sheet to the twelfth rib, or the inner margin in the lowest slice in which the inner margin has been determined by contrast with lung tissue. The RWF module then extends parts of that sheet down the CT image until they encounter the iliac crests posteriorly (towards the bottom of the scan) and laterally (to the right/left of midline), and the pubis anteriorly (towards the top of the scan). The RWF module may use as a tethering criterion the previously identified points which represent cortical bone. Thus, the AIR software may use a right, left, anterior, and posterior approach for extending the RWF sheet from the ribs down to the pelvis. The RWF sheet generated by that process may form a generally ellipsoid or cylindrical shape centered on the center point of the body (as determined by averaging the outer margins of the body wall).

Figure 3:
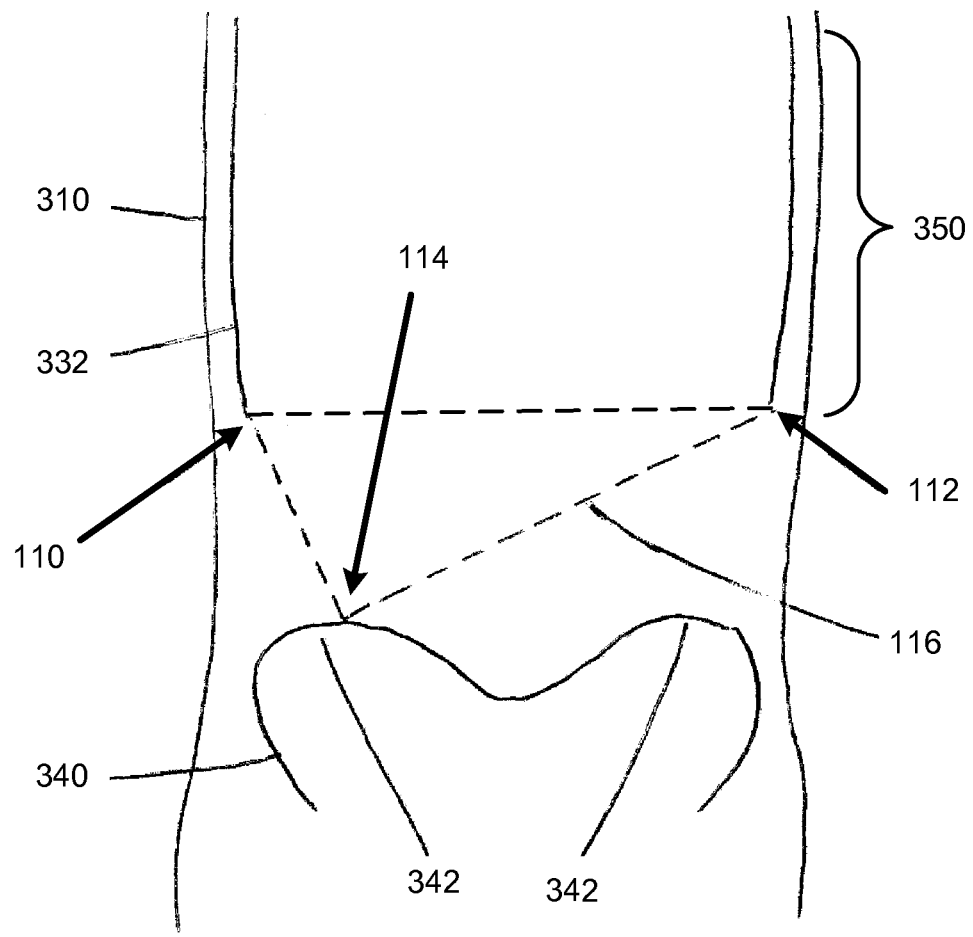
FIG. 3 is line drawing that represents a frontal view of a CT image of the body, with a reverse wire framing line to assist in recognizing the abdominal body wall.

FIG. 3 shows a simplified frontal view of a body to illustrate such an RWF process. The process may include discerning the iliac crests 342 of the pelvis 340 and determining the distance from the bottom of the chest area 350 to the pelvis. In FIG. 3, the two corners 110 and 112 of the RWF sheet 116 have been tethered to the right and left twelfth ribs. In addition, the RWF module has moved another corner 114 of RWF sheet 116 down the CT image until that corner encountered an iliac crest 342 of the pelvis 340. Consequently, the RWF module tethered that corner to that iliac crest. Accordingly, the RWF line segment between points 110 and 114 corresponds to the distance from the bottom of the chest to the pelvis. In addition, the RWF module will extend another corner of RWF sheet 116 down until that point tethers to the other iliac crest.

In addition, as mentioned above, the RWF module may use a similar approach to extend the RWF sheet down the anterior, left, and right sides, to form a generally cylindrical shape connecting the ribs to the pelvis. Thus, the body wall module may use the ribs within the inner margins of the body wall in the upper torso and the iliac crests and pubis of the pelvis to formulate an initial estimate of the inner margin of the body wall in the abdominal area. The points of this RWF sheet lie between the tethered points in the chest and the pelvis. Once this initial estimate is formulated, the body wall module may use the estimate to discern the relatively weak gradient in radiodensity between the muscle in the abdominal body wall and intra-abdominal or subcutaneous fat tissue, the two components of the abdominal body wall inner margin. The AIR software may use that gradient as a tethering condition of the inner margin of the abdomen without excess interference from or confusion with other tissue interfaces.

Figure 4:
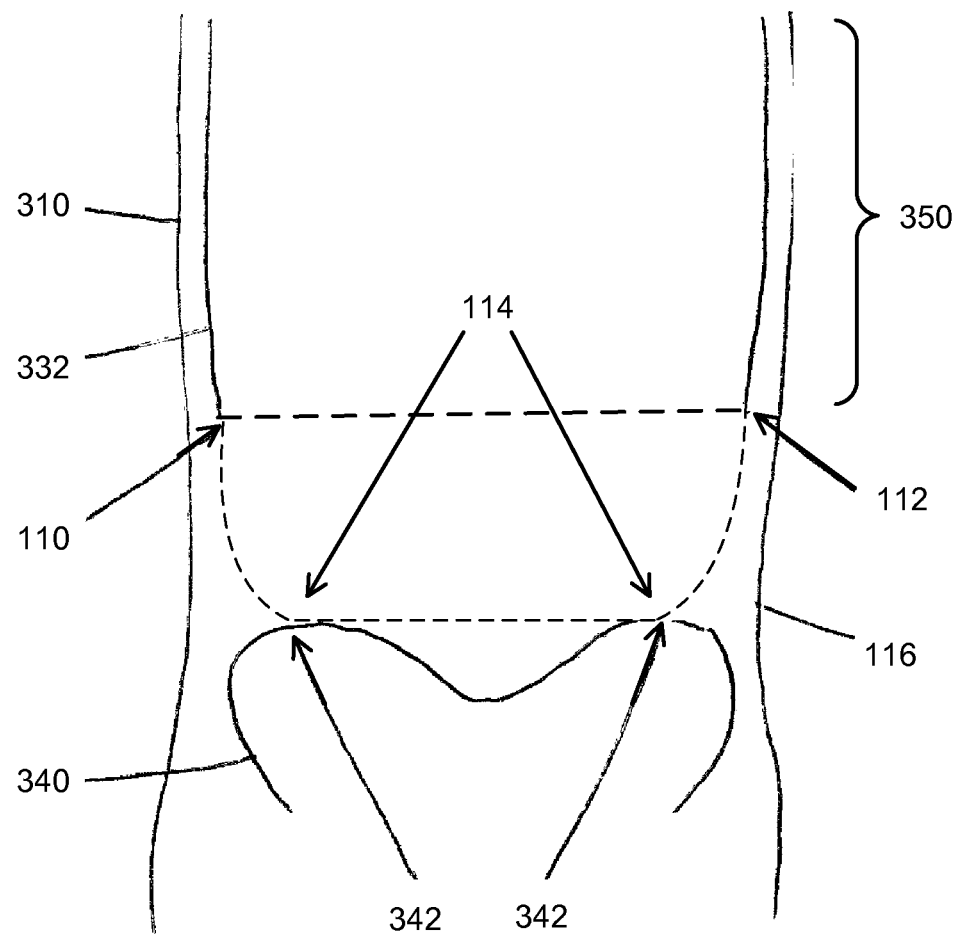
FIG. 4 is line drawing that represents a simplified frontal view of a CT image of the body, illustrating the abdominal body wall determination.

FIG. 4 is line drawing that represents a simplified frontal view of a CT image of the body, illustrating the abdominal body wall determination, in cross section. After discerning the inner margin of the body wall for the lower torso, the AIR software may update the AIR table to identify the relevant voxels as belonging to the inner margin of the body wall.

6. Discerning the Blood Vessels

As shown at block 84 of FIG. 12, the body wall module may also partition each slice for the trunk or torso of the subject into two or more quadrants. In one embodiment, the body wall module partitions each slice of the torso into nine quadrants, as shown in FIG. 1.

FIG. 1 shows a slice of a CT image divided into nine quadrants 300. The central quadrant is considered the first quadrant, and it is surrounded by the other eight quadrants. Each quadrant 300 may contain a portion of the CT image that includes imaging information about the body. The first quadrant may include an area of special interest, as described in greater detail below.

As shown at block 86 of FIG. 12, the AIR software may use the vessel mapping module to discern and identify blood vessels in this CT scan data, starting with the aorta. The vessel mapping module may use one or more subroutines or other modules for this purpose, such as the RWF module for discerning margins, a primary aorta routine for discerning a primary portion of the aorta, vessel tracking algorithms and lumen center point algorithms for discerning blood vessels, etc. Some or all of these modules or subroutines could run on the GPU.

6.1 Finding a Preliminary Reference Point

Figure 13:
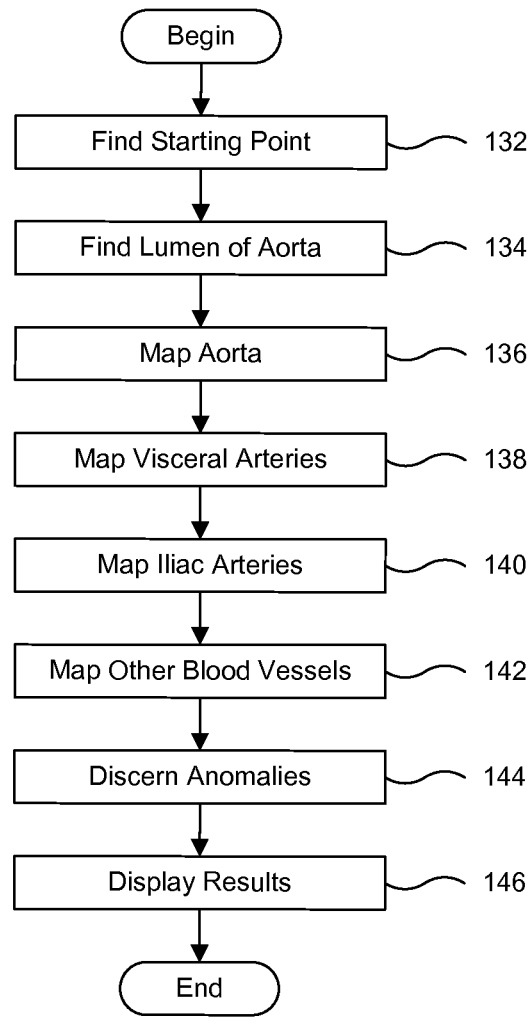
FIG. 13 is a flowchart of an example embodiment of a process for automatically recognizing blood vessels from CT scan data.

FIG. 13 is a flowchart depicting an example embodiment of a process for automatically recognizing blood vessels from CT scan data. As shown at block 132, the vessel mapping module may start by selecting a preliminary reference point to help in locating the aorta. For instance, in one embodiment, the vessel mapping module uses RWF in the spine area of a selected slice (e.g., the first slice), to select the initial reference point.

Figure 5:
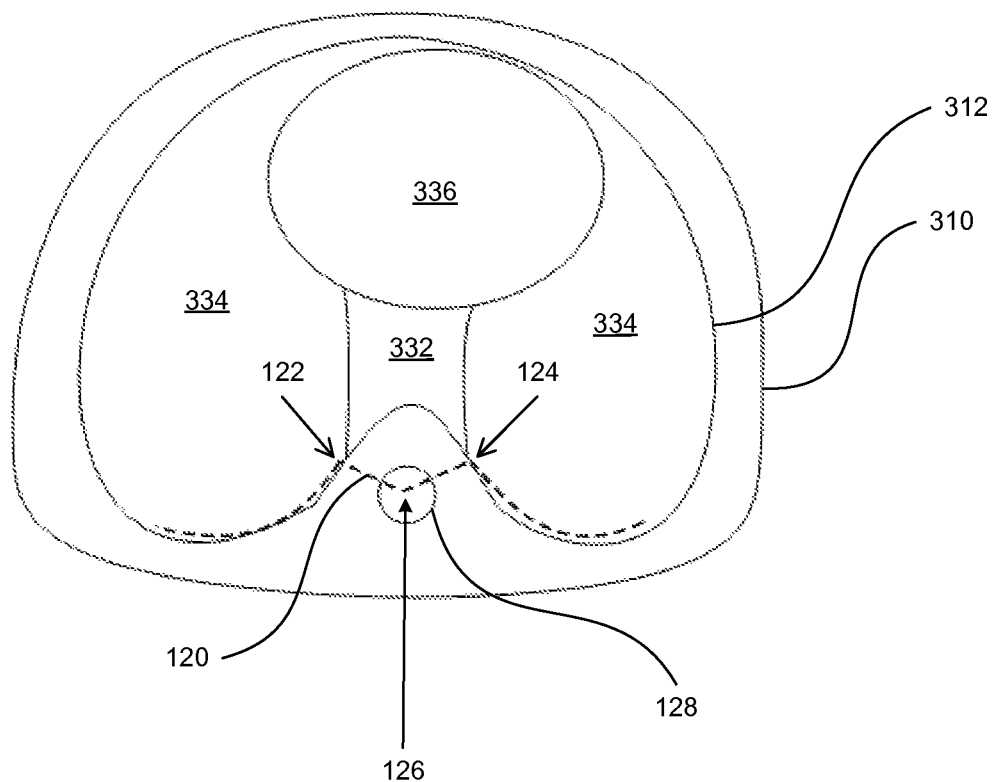
FIG. 5 is line drawing that represents a single slice of a CT image, along with virtual structures used to assist in recognizing the aorta.

FIG. 5 is line drawing that represents a starting slice, along with an RWF line 120 for helping to find the aorta. In one embodiment, the starting slice includes a region containing parts of the posterior mediastinum 332 and spine, and part of the spinal canal 128 (which contains the spinal cord and runs through the vertebrae that make up the spine). FIG. 5 also depicts portions of the inner margin 312 and outer margin 310 of the body wall, the heart 336, and the lungs 334. In addition, the apex 126 of RWF line 120, after the line has been modified as described below, is shown near the center of spinal canal 128.

Before the apex has been formed, the vessel mapping module may start by tethering the two ends of RWF line 120 to the two points 122 and 124 where the lungs meet the inner margin of the body wall, nearest the spine, at the posterior mediastinum. The vessel mapping module may then extend the center of RWF line 120 down into the spine area, forming a V-shape.

In other words, the points to the right and left of the spine are tethered, and in between those points the RWF remains untethered and forms a V-shape, with the apex in the spinal canal. When extending the center of RWF line 120, the vessel mapping module may apply constraints to the untethered parts of the line, as described above. For instance, the distance of each moveable point from an adjacent point of the line may be limited to a specified maximum (e.g., 3 mm). As the points of the line reach their maximum allowed distance from each other and from the tethered end points, the V-shape forms. The apex of the V-shape reliably falls near the center of the spinal canal, which serves as the preliminary reference point 126 for locating the aorta. For instance, the vessel mapping module may use apex 126 as one corner of a volumetric vessel tracking algorithm which is used to find the aortic starting point.

6.2 Discerning the Aorta

Once the vessel mapping module has located this preliminary reference point, the vessel mapping module uses that point to begin mapping the aorta. In particular, as indicated at block 134 of FIG. 13, the vessel mapping module may use the primary aorta routine to discern the lumen of the aorta (i.e., the interior space of the aorta) within a particular area of the scan associated with the preliminary reference point. Specifically, in one embodiment, the primary aorta routine creates a large volumetric analysis cube to analyze the CT scan data in a specified volume across several adjacent scan slices. The primary aorta routine creates this cube to select a certain area of the body represented by the CT scan data. The primary aorta routine creates this cube to the left of the preliminary reference point, for the purpose of discerning the descending thoracic aorta. The volumetric analysis cube is expected to include some of the spine, as well as a segment of the aorta, in all patients (except those with a right sided aortic arch including patients with situs inversus), including patients with abnormally placed aortas. If the descending thoracic aorta is not found in this area, the primary aorta routine shifts the cube across the midline until the descending thoracic aorta is found.

Figure 6:
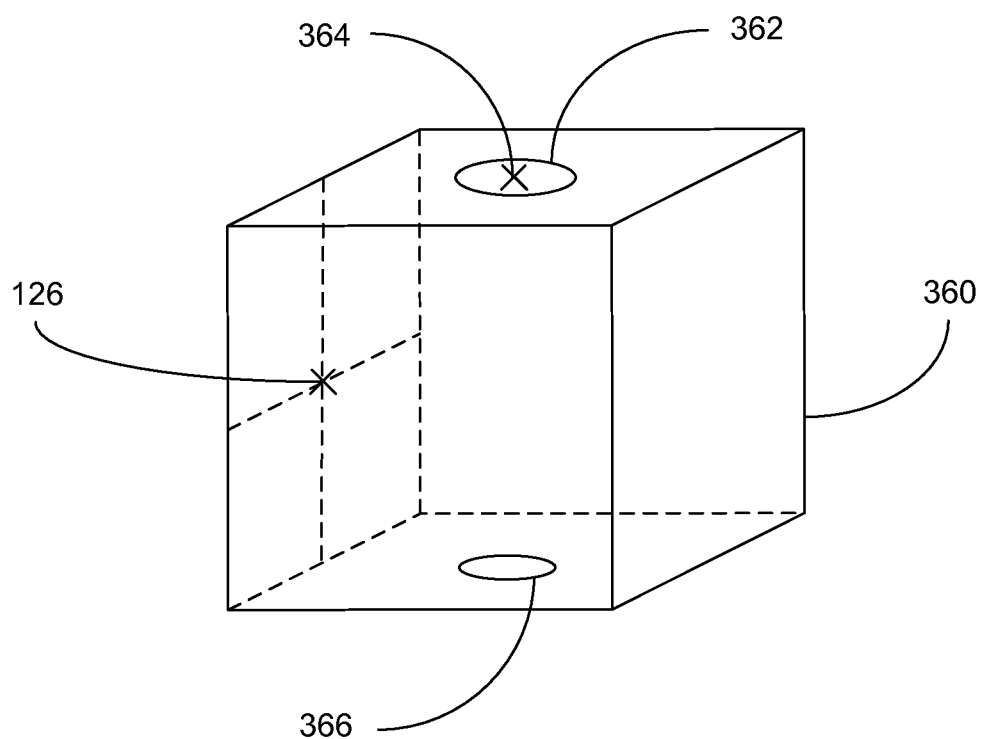
FIG. 6 is a line drawing depicting a volumetric analysis cube used for locating the aorta.

FIG. 6 is a line drawing depicting an example volumetric analysis cube 360 for discerning the descending thoracic aorta. As illustrated, the center of the right face of the cube includes the preliminary reference point 126. For instance, a volumetric vessel flux cube with a size of 128×128×64 voxels may be set up in this area. Thus, the primary aorta routine starts looking for the aorta to the left of the spine on the first slice. Since the volumetric analysis cube is placed to the left of this point, in this frontal view, the cube appears to the viewer's right of this point. The cube in FIG. 6 also shows one candidate aorta cross section 362 at the top and another candidate aorta cross section 366 at the bottom. When, as described below, the volumetric vessel tracking algorithm determines that a candidate aorta cross section matches the aorta, the center 364 of the candidate aorta cross section also marks the center of aortic lumen.

In one embodiment, after creating the volumetric analysis cube, the primary aorta routine uses the volumetric vessel tracking algorithm to search within the cube for an area having (1) a substantially similar or uniform radiodensity (as denoted by HU value) throughout an area with a radius between 1 and 4 cm and (2) substantial continuity in density (as denoted by HU value) with similar areas in a number of adjacent slices further below the slice to which the algorithm is first applied. In particular, potential aortic points or voxels may be identified on the first slice and on the bottom face of the cube. The volumetric vessel tracking algorithm may then attempt to connect the various combinations of starting and ending points. Presumably, the only start and end points which will have continuous contrast density between them will be points which correspond to the aorta.

For instance, in one embodiment, the volumetric vessel tracking algorithm searches the data in the slice corresponding to the top face of the cube for a high-radiodensity structure (e.g., HU values between 200 and 500) with an area approximately equal to that of the aorta (e.g., in an adult, an approximately circular area with a radius of approximately 1.5 cm). The volumetric vessel tracking algorithm may also search the data in the slice corresponding to the bottom surface of the cube for an area of similar size, shape, and radiodensity. These searches may return several candidate areas. The volumetric vessel tracking algorithm may then filter the candidate areas, based on similarity between the size of the top area and the size of the bottom area, and based on location within the body as well as continuity of contrast density voxels. The volumetric vessel tracking algorithm may also use a statistical map of the aorta (or other data from prior successful searches for the aorta in other CT scans) to determine which candidate areas are most likely to represent the actual aorta. The volumetric vessel tracking algorithm may also exclude any candidate areas that do not fall completely within the previously-determined inner body wall. The volumetric vessel tracking algorithm may then determine whether two of the candidate areas, one at the top surface of the cube and one at the bottom of the cube, are continuous with respect to radiodensity throughout the center of the cube.

If such a pair is found, the volumetric vessel tracking algorithm may classify the relevant voxels in the top face of the cube as a cross-section of the lumen of the aorta. The volumetric vessel tracking algorithm may then use a lumen center point algorithm to locate the center of that lumen cross-section. The primary aorta routine may thus discern the lumen of the aorta and the center point of that lumen. In one embodiment, this center point serves as the primary reference point for discerning and identifying blood vessels.

The vessel mapping module may then map the rest of the aorta, based on the entire CT scan data, as indicated at block 136 of FIG. 13. In one embodiment, the vessel mapping module starts with the first slice in which the lumen center point has been located. The vessel mapping module then performs RWF, starting with a circle or loop having a radius less than the radius of the lumen, and centered on the identified center point of the lumen (i.e., the primary reference point). The vessel mapping module then expands the loop until all points of the loop have been tethered or constrained, according to the predetermined boundary conditions for discerning blood vessel lumens. Subsequent slices may also be processed in this manner.

In particular, for large vessels (e.g., the aorta, the iliac arteries, and the arch vessels), the center point of the vessel at position P may be calculated by finding the true axis of the vessel and tracking it sequentially in the direction of the vessel. In these large vessels, a cylindrical wire frame is created which extends along the calculated axis of the vessel. The points of the wire frame are moved radially outward from the center point with the constraint that a given point should not have a radial distance from the center point which differs from its adjacent points by greater than a fixed amount. The program may search for voxels which have been previously identified as extrema points and have at least N voxels radially outward with HU below contrast and M voxels radially inward with HU above the threshold for contrast.

Figure 7:
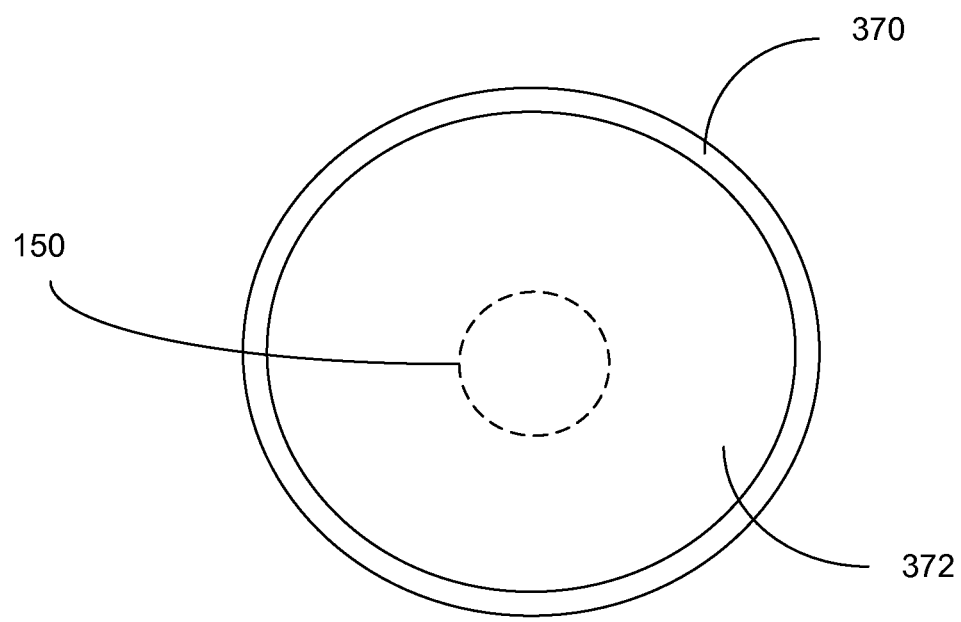
FIG. 7 is a line drawing depicting a cross section of the aorta.

FIG. 7 shows a cross section of the aorta including the wall of the aorta 370, the lumen of the aorta 372, and an RWF circle 150 used to determine the boundary of the lumen (i.e., the inner margin of the vessel wall). The vessel mapping module expands the RWF circle until an expected radiodensity (e.g., HU=1200 to 1500) is reached, or the constraint is met. Where the boundary condition encountered, the circle is fixed. When the entire circle is fixed, the lumen is determined. The vessel mapping module may then use the lumen center point algorithm to determine the center point of the aorta in that slice.

Then, the vessel mapping module similarly determines the inner margin of the lumen and center point of the lumen in the next slice down. This process may continue until the vessel mapping module reaches the level of the iliac crests, thereby generating a wire-frame model of the aorta. Thus, the vessel mapping module automatically determines which voxels in a CT scan belong to the aorta. In addition, the center point data may be saved for use in subsequent operations.

6.3 Discerning the Visceral Arteries

The vessel mapping module may analyze the wire-frame model of the aorta for clusters of non-tethered points, as such clusters represent potential branch points or ostia for the primary visceral arteries: the celiac trunk, the superior mesenteric artery, the inferior mesenteric artery, and the left and right renal arteries. For example, the vessel mapping module may apply a vessel branch point algorithm to the aorta lumen margin data, to generate a list of possible starting points for the primary visceral branches from the aorta.

Figure 8A:
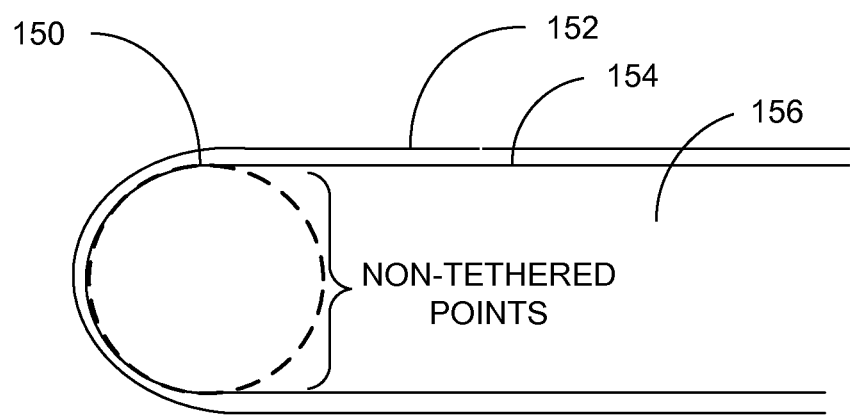
FIGS. 8A and 8B are line drawings depicting cross sections of the aorta at two different branch points.

FIG. 8A depicts a cross section of the aorta at the branch point of a branch at approximately a 90 degree angle with the axis of the aorta, with the aorta and the RWF circle 150 used to determine the aortic lumen on the left of the figure and the branch on the right. RWF circle 150 has been tethered on about half of its circumference, determining the lumen boundary of the beginning part of the branch. But where the branch leaves the aorta, there is a cluster of non-tethered points. As shown, the branch includes an outer arterial wall 152, an inner arterial wall 154, and a lumen 156.

Figure 8B:
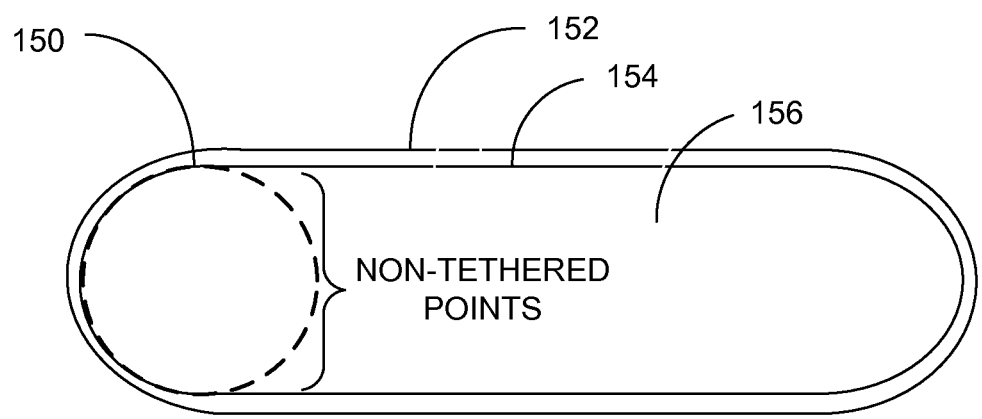

FIG. 8B shows a cross section of the aorta near the bifurcation into the common iliac arteries, with the RWF circle used to determine the aortic lumen on the left of the figure and the widening of the lumen caused by the bifurcation on the right. The RWF circle 150 has been tethered on about half of its circumference, determining the lumen of the beginning part of the bifurcation. But where the bifurcation widens the lumen, there is a cluster of non-tethered points.

In one embodiment, the vessel mapping module uses expected characteristics of the primary visceral arteries (e.g., the relative order, the approximate size, and the branch direction) to search for those arteries. For instance, the vessel mapping module may search for the ostia of the celiac trunk, the superior mesenteric artery, the inferior mesenteric artery amongst the clusters of non-tethered points which are positioned anteriorly within the aorta. Cluster of points originating to the left and right of midline are considered potential origins for the left and right renal arteries. Specifically, the wire frame technique will identify all the branches of the parent vessel including the paraspinal arteries located posteriorly and accessory/ectopic renal arteries located caudally with respect to the expected region of the renal arteries. And the vessel mapping module may analyze whether a candidate branch point for each artery branches in the expected direction (e.g., in an anterior direction for the celiac trunk, or a lateral direction for the renal arteries.) After identifying good candidates for the primary visceral arteries, the vessel mapping module may use neural network modeling and pattern matching with model anatomies to confirm the identity of those arteries. The vessel mapping module may also use sequential volumetric vessel analysis to confirm those identities, and to map additional arteries. Within the volumetric regions, a directed virtual angiogram can be performed at the point where a vessel enters the region of interest. This process allows for tracking an arbitrarily large/small vessel as well as vessels which terminate within the volumetric region.

For example, as indicated at block 138 of FIG. 13, the vessel mapping module may perform vessel tracking on each artery that starts at each of the primary branches, to generate a list of potential branch points of primary branches from each primary visceral artery. An artery which branches directly from a primary visceral artery may be referred to as a secondary visceral artery. The primary branches from the celiac axis include the left gastric artery, the splenic artery, and the common hepatic artery. The vessel mapping module may segment this list of potential branch points into sub-lists of potential branch points for each secondary visceral artery.

The vessel mapping module may also perform vessel tracking in the expected direction of each sub-branch, and may assign a sequential number to the branch points identified by the vessel tracking. The vessel mapping module may use this data to generate sequential numbering for all branches and sub-branches, with the number sequence indicating how close a branch is to the aorta. For instance, branch point number 1 might identify the branch point or ostium for the celiac trunk, and branch point number 1.1 might identify the first branch point detected along the celiac trunk.

The term "virtual angiogram" may be used to refer to this kind of automatic vessel tracking process, and to the results from such a process. In one embodiment, the vessel mapping module uses one or more volumetric vessel tracking algorithms to perform virtual angiograms. For purposes of this disclosure, the terms "volumetric vessel tracking" and "volumetric vessel analysis" refer to techniques for discerning the lumen of a blood vessel, based at least in part on data pertaining to adjacent parts of the blood vessel and qualities of those adjacent parts, such as size, shape, and density. Such techniques may also be used to discern simple and complex branch points of a blood vessel. More details regarding an example volumetric vessel tracking algorithm are provided below, under the heading "virtual angiogram."

6.4 Discerning the Iliac Arteries

The vessel mapping module may then use volumetric vessel analysis to analyze the lower end of the aorta, as determined by the level of the iliac crests, to determine the bifurcation of the aorta into the common iliac arteries, as indicated at block 140. The vessel mapping module may then perform additional volumetric vessel analyses in conjunction with virtual angiograms to evaluate the common iliac arteries for their respective bifurcations into the external and internal iliac arteries. Once these four branches are identified, the vessel mapping module may use the RWF module to track those arteries to their terminations.

In one embodiment, the vessel mapping module uses the vessel branch point algorithm to make initial determinations regarding the locations of ostia for the common iliac arteries and the external and internal iliac arteries. The vessel branch point algorithm bases its initial determination on the lumen cross-sectional size of the potential starting points of the branches, together with the positions of those branches, with respect to each other. The vessel mapping module may also compare analysis results with anatomical models to assist in identification of these arteries, At this point, the vessel mapping module typically will have discerned candidates for the primary visceral arteries, the secondary visceral arteries, and the iliac arteries. The vessel mapping module may then analyze the additional ostia originating from the aorta, to determine whether those branch points are for arteries that have not yet been included in the analyses.

6.5 Discerning Other Blood Vessels

As indicated at block 142, the vessel mapping module may use volumetric vessel analysis on each of the branch starting points that hasn't already been identified as a candidate for a primary visceral artery, a secondary visceral artery, or an iliac artery. In one embodiment, the vessel mapping module uses narrower radiodensity limits (e.g., HU values from 250 to 550) than those used for the aorta. Using these narrower radiodensity limits, the virtual angiogram returns the points in the CT image that are within the lumens of arteries. Further, the virtual angiogram may exclude points that have been identified as bone or body wall, even if those points meet the criteria used to identify arteries.

6.6 Virtual Angiogram

In a conventional angiogram, a catheter or tube is inserted into the aorta, and the end of the tube is placed at the ostium of a vessel (e.g. right renal artery). Contrast is then injected and sequential static images (2-8 frames per second) are captured. These images serve as a video clip which shows filling of the vessel in the direction that blood would actually flow. According to the present disclosure, a virtual angiogram starts at a point or voxel that has been identified as part of an ostium, and assigns a number (e.g., #1) to that voxel. The virtual angiogram than assigns the next number (e.g., #2) to the voxels surrounding the initial point in a selected direction (e.g., downstream, or in a direction away from blood vessels that have already been mapped or identified), provided those adjacent points are within a suitable range of density values and immediately adjacent to the initial point. The virtual angiogram then repeats that process such that an arbitrary point in the vessel will be identified as (n+1). This process thus mimics the actual flow of blood in the vessels.

Figure 14:
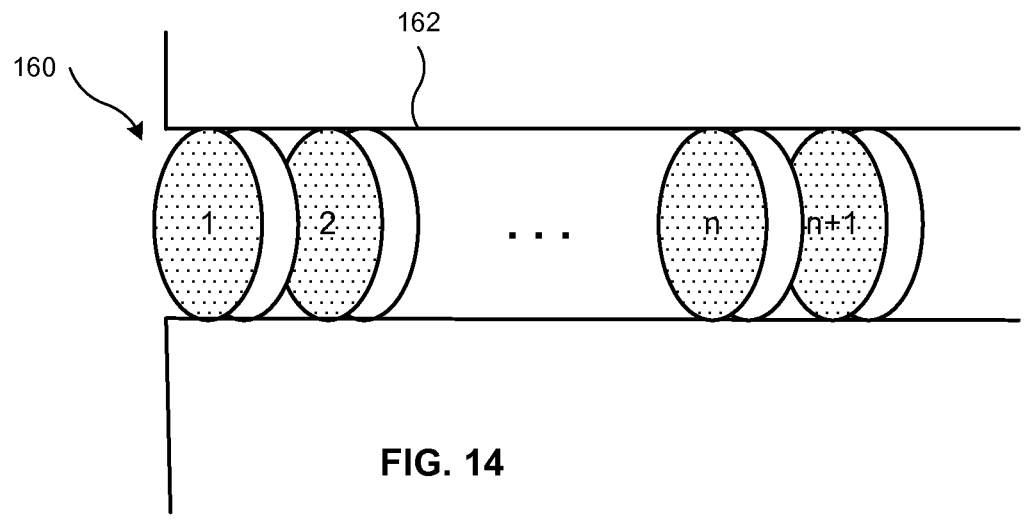
FIGS. 14 and 15 are line drawings that illustrate the assignment of consecutive numbers to adjacent parts of blood vessels, according to an example virtual angiogram process.
Figure 15:
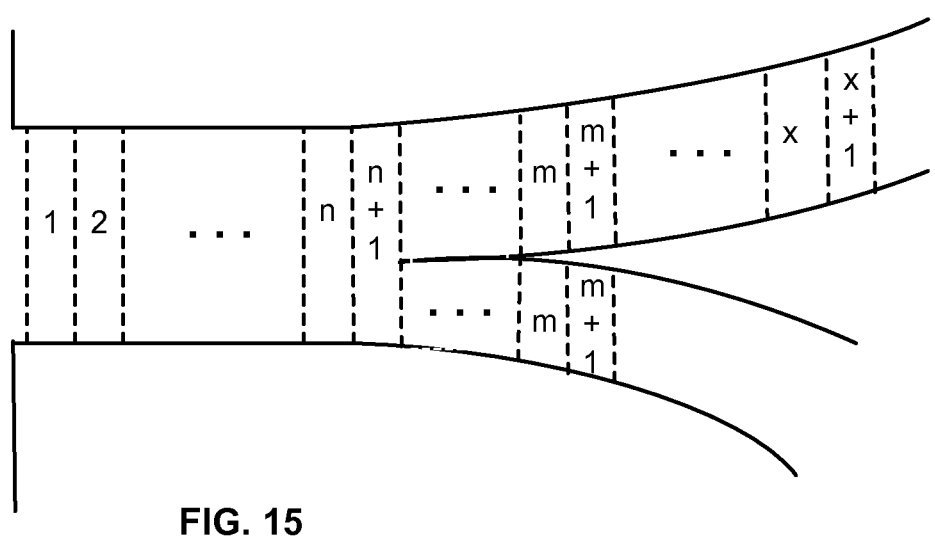

FIGS. 14 and 15 are line drawings that illustrate the assignment of sequential numbers to consecutive parts of blood vessels, according to an example virtual angiogram process. In particular, FIG. 14 illustrates that the vessel mapping module assigns the number 1 to a first region at the ostium 160 of a branch 162, the number 2 to the next region, etc., including regions n and n+1. FIG. 15 provides a similar illustration for a more complex blood vessel. For instance, FIG. 15 shows that the vessel mapping module can continue to assign consecutive numbers (e.g., m, m+1, x, x+1, etc.) to portions of a blood vessel, even after that blood vessel has split into two or more sub-branches. The vessel mapping module may thus track all possible branching patterns automatically. The vessel mapping module may then use the data from this virtual angiogram to reconstruct the path of the visceral vessels, for instance.

In addition, the volumetric vessel tracking algorithm (VVTA) may analyze three-dimensional space (across slices), including attributes of the RWF, to discern ostia. For example, the VVTA may select a reference point at or near the center of a lumen to serve as the primary reference point. The VVTA may then proceed from that point to discern clusters of untethered points in the wire frame, such as the cluster of untethered points depicted in FIG. 8A. For each cluster of untethered points with a size that equals or exceeds a predetermined threshold (e.g., 10 mm), the VVTA may add that cluster to the list of potential branch points, in recognition of the possibility that the untethered points reflect the ostium or lumen of a new vessel. The VVTA may determine the size of each cluster of untethered points by measuring the surface area covered by those untethered points. On other words, the non-tethered points reflect gap in the cylindrical surface of the aorta, and the VVTA measures the surface area or cross section of that gap.

In one embodiment, the VVTA assigns a different number "n" to each cluster. The VVTA then assigns the number "n+1" to the voxels immediately adjacent to the first cluster, the number "n+2" to the next set of voxels out, etc. This process continues for a specified number ("m") of times until there is a set of points assigned the number "n+m." However, the VVTA only includes voxels in this process if the voxels have HU values within a specified radiodensity range and gradient values below a specified threshold. Also, the VVTA excludes voxels which have already been classified as belonging to the parent artery (i.e., the artery containing the potential branch point at issue). Consequently, when a potential branch point actually leads into an artery, the above analysis will result in identification of a generally tube-shaped structure that intersects the cluster of points assigned the number "n." By reference to the sequentially numbered set of voxels meeting the above criteria, the VVTA classifies this generally tube-shaped structure as the lumen of a newly discerned artery.

The VVTA may assign sequential numbers to all potential lumen points through the course of the newly discovered artery, according to the distance of each point from the origin of that artery. The VVTA may also analyze such a structure to determine the direction taken by the artery, and the approximate center of the artery.

Figure 9A:
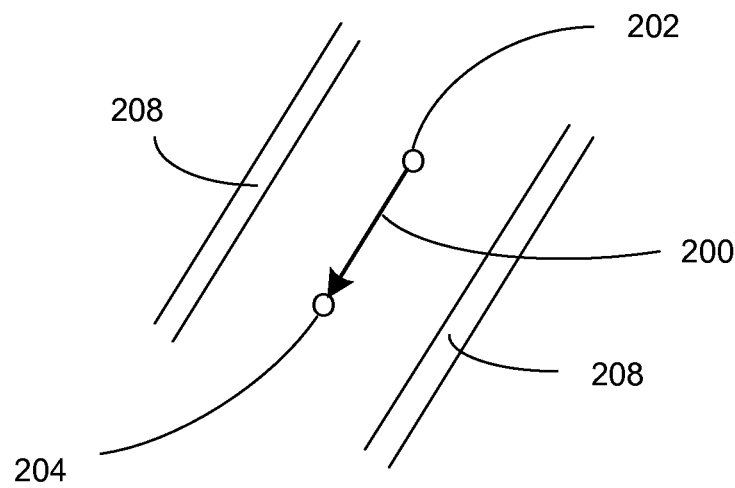
FIG. 9A is a line drawing depicting two adjacent lumen center points used to identify an arterial axis.

FIG. 9A is a line drawing depicting a cross section of any artery with an arterial wall 208. Also depicted are two adjacent lumen center points 202 and 204, and a vector 200 from one center point to the other, such that the vector coincides with the arterial axis. Once the VVTA finds two adjacent voxels at the center of the structure, the VVTA may compute a vector joining those two center points. This vector approximates the direction of the true axis of the artery at the location of the two points. The plane perpendicular to this vector coincides with the cross-section of the artery at the location of the two points.

Figure 9B:
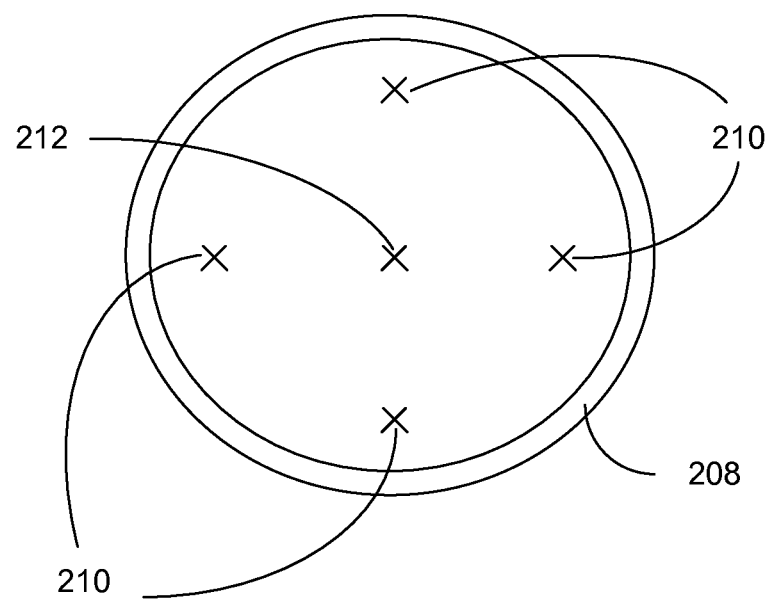
FIG. 9B is a line drawing depicting a cross section perpendicular to the arterial axis shown in FIG. 9A, with reverse wire framing points used to determine an arterial lumen boundary.

FIG. 9B shows the arterial cross section at a point along the vector from FIG. 9A and perpendicular to that vector. Also shown are four RWF points 210, which may constitute a four-point reverse wire frame. Eight points, or other numbers of points, may be used in other embodiments. In one embodiment, the VVTA introduces those points at the location of the two adjacent lumen center points, near the center of the lumen within the expected lumen cross sectional area, and the VVTA then moves the four points outward from the axis 212 until they are tethered to the lumen at the inner margin of the wall of the artery, according to expected radiodensity values. The VVTA may then compute the cross-sectional diameter of the artery at this location, based on the four-point reverse wire frame. The VVTA may repeat this kind of analysis for all adjacent lumen center points, in order to detect and establish a wire frame for the entire arterial lumen and therefore the entire artery.

Furthermore, the vessel mapping module may use the VVTA to discern all arteries leading from all potential branch point, down to branch points of a predetermined diameter. The vessel mapping module or the VVTA may also use the lumen center point algorithm to generate a list of candidate center points for each artery.

The vessel mapping module may then determine which potential center points should be considered actual center points. In one embodiment, the vessel mapping module uses a neural network computational model to determine which candidate center points should be considered actual center points. For example, the vessel mapping module may load the list of candidate lumen center points into the GPU, and the vessel mapping module may run a neural network algorithm to determine the valid arterial branch points, lumen center points, and such.

The vessel mapping module may also compare the candidate branch points and arteries against anatomical models to evaluate the validity of the results. For instance, the vessel mapping module may use a set of anatomical models that include common normal varieties of the arterial system to guide the analysis of the arteries as described herein. For example, the vessel mapping module may compare the anatomical models with results from the analysis to verify those results, or to select between two or more different potential interpretations of the scan data.

In addition, if any analysis results do not match the anatomical models, the vessel mapping module may prompt a user to provide input indicating whether or not the analysis results should be added to the database of potential variants.

Also, in one embodiment, the vessel mapping module checks to determine whether any artery remains unidentified in a CT image. If a lumen has not been determined for a particular artery, the vessel mapping module may search for that artery in the CT image, based on data regarding the organ at which the artery is known to terminate. For instance, if the hepatic artery has not been identified in the CT image, the vessel mapping module may looked for it in the region of the CT image between the liver and the aorta.

After determining which voxels belong to which arteries, the vessel mapping module may update the AIR table to identify those voxels accordingly (i.e., to identify the relevant voxels as belonging to particular blood vessels). In addition, a wire frame model of the vessel is also kept in memory for guiding further steps, such as the organ analysis.

Furthermore, the AIR software may automatically analyze the resulting data to determine aberrancies such as aneurysms and areas of luminal narrowing, as indicated at block 144 of FIG. 13. The AIR software may display the results on an output device, as indicated at block 146. The results may include graphical and/or textual representations of the identified anatomical structures, as well as information pertaining to any suspected anomalies, to alert a user such as a radiologist of potential pathology. The graphical representation of the identified anatomical structures may include a wire frame of the inner wall of all arteries that have been discerned in the CT image. This wire frame may be displayed graphically as a virtual angiogram, in other words, as an animation or image that resembles and serves the same purposes as a traditional angiogram.

As indicated, in one embodiment vessel tracking is performed after the bone identification and body wall identification algorithms have completed, to ensure that there is no contamination by medullary bone points, which have similar density to contrast.

7. Discerning the Organs

Once the vessel mapping module has discerned and identified some or all of the vascular system from the CT image, the AIR software may use the vascular system as a roadmap to determine the locations of the organs in the CT image, and to discern the outer margins of those organs, as indicated at block 88 of FIG. 12. In one embodiment, discerning organs involves a combination of performing a virtual angiogram to "enhance" the organ and comparing that result with an anatomical model of the particular organ.

To start, the organ identification (ID) module may use the arterial tree as a map for locating visceral organs at or near the end of particular arteries. For enhancing organs, the organ ID module than performs a virtual angiogram to determine the points which are part of the target organ that have taken up the injected contrast. Once the virtual angiogram has been performed on the organ, one or more 3D reverse wireframes are constructed to determine the outer margin of the organ, as described below. The AIR software uses the results of the virtual angiogram along with the RWFs as a framework for comparing the results of the current scan with one or more corresponding anatomical models. In other words, the virtual angiogram produces a set of points which are likely to be in the organ of interest. The RWF is applied with the tethering condition of finding a point identified by the virtual angiogram. Then the results of the RWF are modified by applying the anatomic model, which will let the program know if there are obviously extraneous points or if the organ deviates significantly from the normal morphology of the organ.

For example, the organ ID module may analyze the right renal artery to find its end, the right renal hilum, which is necessarily at or near the right kidney. The organ ID module may then perform a virtual angiogram starting at the right renal hilum to identify a set of points which are likely to be in the right kidney.

The organ ID module may then introduce a RWF in the shape of a three-dimensional ellipsoid around the points at the end of the right renal artery. This ellipsoid is significantly smaller than a kidney. The RWF is then expanded outward until predetermined boundary conditions are met. For example, the organ mapping module may tether the RWF when there are no voxels radially outward from the current position that have been identified by the virtual angiogram as representing points in the organ. In other words, the RWF may be expanded out to the last voxels that are "enhancing" from the right renal artery, and then tethered at those voxels. To be enhancing from an artery, a point must have a substantially similar radiodensity as that artery and must be connected with that artery directly or by points that have a substantially similar radiodensity as that artery. Alternatively, the organ mapping module may tether the RWF when there are no points radially outward from the current position that have been identified by either the virtual angiogram or the anatomical model as representing points in the organ.

Furthermore, the organ mapping module may apply a second RWF to the organ, starting beyond the expected boundaries of the organ with an ellipsoid that is significantly larger than the expected margins of the kidney. The organ mapping module may then collapse that RWF inward until predetermined boundary conditions are met, such as the condition that a point is enhancing from the corresponding artery (e.g., the right renal artery), or the point corresponds to the margin of a kidney, according to the anatomical model. In other words, the bone mapping module may tether the points of the second reverse wire frame in response to determining that a point in the RWF corresponds with a point which has been identified as part of the organ by the virtual angiogram or by the anatomical model. Other boundary conditions may be used in other embodiments.

However, for both RWFs, the organ ID module may exclude from consideration as a potential part of the organ all points in the CT image that have been identified as part of the body wall, as bones, as other organs, or as blood vessels, since those structures may have similar radiodensities as parts of the organ being discerned (e.g., the kidney) or might otherwise be confused with that organ.

Once both RWFs have been created, the bone mapping module may reconcile them into a final RWF by utilizing an anatomic model which has the contour and morphology of the organ of interest. The application of the anatomic model allows for the exclusion/inclusion of points which are indeterminate based on the RWF analysis.

Consequently, the organ ID module may update the AIR table to identify the relevant voxels as belonging to the determined organ (e.g., right kidney). The organ ID module may use this same kind of process to determine the other visceral organs in a CT image.

As indicated at block 90, the organ ID module may also evaluate the organs for anomalies or pathology. For example, the organ ID module may compare the organs, as determined in the CT image, with anatomical models of normal and abnormal organs to assess the imaged organ for abnormalities (i.e., variations from normal anatomy). Such assessment may be performed, for example, by using neural network modeling to filter the CT image data of the determined organ, based on anatomical models of normal and abnormal organs.

The organ ID module may then output the results of the organ mapping and the analysis for anomalies or pathology, as indicated at block 94. Alternatively, the AIR software may wait until the body margins, bones, blood vessels, and organs have been discerned before displaying the results.

In addition, once the AIR software has identified the organs, if any blood vessels were not found, the AIR software may use the organs as a map to find the missing blood vessels. For instance, rather than starting at an ostium to find an artery that leads to an organ, the AIR software may start at the organ to locate that artery. For instance, the AIR software may perform a sequence of attempts to identify the initial location of the artery at the organ, guided by knowledge obtained from prior studies in which the artery and organ were successfully located.

In one embodiment, the AIR software presents the results of the determination of the outer margin of the body, the inner margin of the body wall, the bones, the arteries, the organs, and the evaluations for anomalies, or some part of those results. As indicated at block 96, the AIR software may also provide a user interface that allows a user to validate, confirm, or reject some or all of the results. The AIR software may also save the results to one or more data files for future use, as indicated at block 98. Thus, the AIR software may increase the pool of anatomical models available for use in automatically analyzing subsequent CT scans. In one embodiment, the AIR software stores data concerning normal anatomy into one database, and data concerning abnormal anatomy into another database.

Further details concerning one or more example embodiments of algorithms or software modules are provided below.

Appendix A involves a reverse wireframing algorithm for discerning or encompassing anatomical structures. In this class of algorithm, a sequence of mobile points is defined, though the motion is constrained by the position of the adjacent points. For instance, as described above with regard to FIG. 5, when a wire frame is dropped down onto the spine and ribs, the algorithm may cause parts of the wire frame to be tethered by the ribs, while adjacent point have constrained freedom of motion.

Various conditions are defined for locking points in place spatially which will stop further movement of those points (essentially tethering them) and limiting the movement of the adjacent point(s). An analogy would be dropping a bed sheet on top of a pillow. As the sheet drops, points that hit the pillow become fixed, while the adjacent parts continue to fall until they come in contact with the bed.

This class of algorithms is also used in identifying the outer margins of the body wall, as well as defining the inner margins of vessels. The following portion of code is an example of the tethering conditional used to determine the inner margins of the aortic lumen. The wire frame itself is defined as a quadruply linked list (Encompass_List) with element currn-ode/head/tail/len. Each element of the list has a 3D position (x, y, z) as well as value (fixed) which signifies whether or not the point is tethered.

Appendix B involves a volumetric vessel flux module or algorithm. This is a class of functions which take as input a 3D point and a spatial direction. The initial spatial point is assumed to be a random point within a vessel. The algorithm then creates a volumetric element which abuts that point and projects in the predefined direction. The five remaining surfaces (not including the one containing the original point) are analyzed for points with similar characteristics to the initial point. A vessel evolution algorithm may be used for this purpose. The points which match the initial point's characteristics are put in lists of potential vessel branches. The points are then coalesced and analyzed to determine which grouping of points represents a coherent vessel lumen and what the center point of that vessel is. A coherent point algorithm may be used for this purpose. The volumetric vessel tracking algorithm may be called recursively to ensure that branch points down to a predetermined size or resolution (e.g., 4 mm) are identified.

An analogy would be having a pipe go into a box and then split into two pipes. Those two resultant pipes must pass through at least one of the wall of the box to be identified. The control logic in Appendix B is one implementation of this type of analysis. The control logic takes as input a starting point and a spatial direction.

The following comments fit where labeled in the appendixes.

Comment A:

The motion function for the wire frame: what to do for the various possibilities of inter node distance, etc.

Comment B:

Cycle over the region of interest and if the point is in a wall of the cube, then check it for potential point (that meet the conditional).

Comment C:

Get the data regarding this point from the global data structure representing the scan data (as discussed above).

Comment D:

Sort the resultant list of potential points into the respective wall that they come from.

Comment E:

Now that the points are in separate lists for each of the potential walls, order the elements of those lists in terms of proximity. The purpose of this step is to facilitate the next algorithm. There is a separate function which performs this sorting.

Comment F:

This portion of the algorithms is important in this analysis as well as in the determination of braches from the aorta. It requires that the data be spatially clustered (as performed by the previous step). It calculates an N×N matrix of distances between each point in the list and every other point. If a distance is greater than a predefined limit, then the value is set to 0. The end result is that if you take only half of the elements (one side of the n equals m line) then points that are sequential in the list and separated spatially will end up with all zeros for distance. Between the last point in cluster A and the first point in cluster B. This process then allows for clustering of points and determination of candidate point. The number of contiguous points is proportional to the cross sectional surface are of the vessel as it crosses the plane of the cube.

Comment G:

The resultant data is returned to the function that called it.

CONCLUSION

In light of the principles and example embodiments described and illustrated herein, it will be recognized that the described embodiments can be modified in arrangement and detail without departing from such principles. Also, although the foregoing discussion has focused on particular embodiments, other configurations are contemplated as well. Even though expressions such as "in one embodiment" "in another embodiment," or the like may be used herein, these phrases are meant to generally reference embodiment possibilities, and are not intended to limit the invention to particular embodiment configurations. As used herein, these terms may reference the same or different embodiments, which may easily be combined into additional embodiments. For instance, some components are described above as using RWF lines for operations such as discerning margins of body parts. It should be understood that some or all of those components may use the RWF module to perform those operations.

Similarly, although example processes have been described with regard to particular operations performed in a particular sequence, numerous modifications could be applied to those processes to derive numerous alternative embodiments. For example, alternative embodiments may include processes that use fewer than all of the disclosed operations, processes that use additional operations, processes that use the same operations in a different sequence, and processes in which the individual operations disclosed herein are combined, subdivided, or otherwise altered.

Alternative embodiments of the invention also include machine-accessible media encoding instructions for performing the operations of the invention. Such embodiments may also be referred to as program products. Such machine-accessible media may include, without limitation, storage media such as floppy disks, hard disks, CD-ROMs, ROM, and RAM. Instructions and other data may be stored locally and/or remotely for access by single or multi-processor machines.

It should also be understood that the hardware and software components depicted herein represent functional elements that are reasonably self-contained so that each can be designed, constructed, or updated substantially independently of the others. In alternative embodiments, many of the components may be implemented as hardware, software, or combinations of hardware and software for providing the functionality described and illustrated herein. The hardware, software, or combinations of hardware and software for performing the operations of the invention may also be referred to as logic or control logic.

Also, this disclosure uses certain terms to refer to particular system components and configurations. However, as one skilled in the art will appreciate, different companies may refer to the same component by different names. It should therefore be understood that, for purposes of comparing different components, the component names may be insignificant, compared to more relevant aspects, such as the functionality provided each component.

Also, unless otherwise specified, terms such as "coupled," "coupleable," and "coupling" are intended to include both direct and indirect connections. Thus, if a first device couples to a second device, that connection may be through a direct electrical or wireless connection, or through an indirect electrical or wireless connection, via one or more other devices and/or connections.

In view of the wide variety of useful permutations that may be readily derived from the example embodiments described herein, this detailed description is intended to be illustrative only, and should not be taken as limiting the scope of the invention. What is claimed as the invention, therefore, are all implementations that come within the scope and spirit of the following claims, and all substantial equivalents to such implementations.

APPENDIX A

Reverse Wireframing (Encompass Algorithm)

```
rad_pos.x=ftoi(Line→currnode→rad);   rad_pos.y=ftoi
   (Line→currnode→angle); //the position of the current
   node
prad_pos.x=ftoi(Line→currnode→prev→rad);
   prad_pos.y=ftoi(Line→currnode→prev→angle); //the
   position of the previous node
nrad_pos.x=ftoi(Line→currnode→next→rad);
   nrad_pos.y=ftoi(Line→currnode→next→angle); //the
   position of the next node
brad_pos.x=ftoi(P_Line→currnode→rad);
   brad_pos.y=ftoi(P_Line→currnode→angle);
prad_diff=prad_pos.x−rad_pos.x; nrad_diff=nrad_pos.x−
   rad_pos.x;
Curr=Profile[rad_pos.x+rad_pos.y*32];
nrad_diff=nrad_pos.x−rad_pos.x; //calculate the distance
   between the current node and the next node
prad_diff=prad_pos.x−rad_pos.x; //calculate the distance
   between the current node and the previous node
brad_diff=brad_pos.x−rad_pos.x;
//Comment A//
   if(Line→currnode→prev→fixed>=1        &&
      Line→currnode→next→fixed>=1)
      {cnt++;
      Line→currnode→rad=rad_pos.x;
      Check_Branch_Point(Profile, Line, rad_pos);}
   else if(prad_diff>=0 && prad_diff<wobble && nrad_
      diff>=0      &&     nrad_diff<wobble     &&
      brad_diff>=i_wobble)
      {rad_pos.x+=1; cnt++;
      Curr=Profile[rad_pos.x+rad_pos.y*32];
      FWD=Profile[rad_pos.x+1+rad_pos.y*32];
      FFWD=Profile[rad_pos.x+2+rad_pos.y*32];
      BKWD=Profile[rad_pos.x−1+rad_pos.y*32];
      BBKWD=Profile[rad_pos.x−2+rad_pos.y*32];
      Line→currnode→rad=rad_pos.x;
      if(Curr.z>0 && FWD.z==0 && FFWD.z==0 &&
         BKWD.z>0      &&      BBKWD.z>0)
         {Line→currnode→fixed=1;}
      else if(Curr.z==0 && FWD.z==0 && FFWD.z==0)
         {Line→currnode→fixed=1;}
      else if(Curr.z==0 && BKWD.z==0 && BBK-
         WD.z==0){Line→currnode→fixed=1;}}
   else if(prad_diff>=0 && prad_diff<wobble && nrad_
      diff<0      &&     nrad_diff>−wobble     &&
      brad_diff>=i_wobble)
      {rad_pos.x+=1; cnt++;
      Curr=Profile[rad_pos.x+rad_pos.y*32];
      FWD=Profile[rad_pos.x+1+rad_pos.y*32];
      FFWD=Profile[rad_pos.x+2+rad_pos.y*32];
      BKWD=Profile[rad_pos.x−1+rad_pos.y*32];
      BBKWD=Profile[rad_pos.x−2+rad_pos.y*32];
      Line→currnode→rad=rad_pos.x;
      if(Curr.z>0 && FWD.z==0 && FFWD.z==0 &&
         BKWD.z>0      &&      BBKWD.z>0)
         {Line→currnode→fixed=1;}
      else if(Curr.z==0 && FWD.z==0 && FFWD.z==0)
         {Line→currnode→fixed=1;}
```

```
        else if(Curr.z==0 && BKWD.z==0 && BBK-
            WD.z==0){Line→currnode→fixed=1;}}
        else if(prad_diff<0 && prad_diff>=-wobble && nrad_
            diff>=0    &&    nrad_diff<wobble    &&
            brad_diff>=i_wobble)
        {rad_pos.x+=1; cnt++;
            Curr=Profile[rad_pos.x+rad_pos.y*32];
            FWD=Profile[rad_pos.x+1+rad_pos.y*32];
            FFWD=Profile[rad_pos.x+2+rad_pos.y*32];
            BKWD=Profile[rad_pos.x-1+rad_pos.y*32];
            BBKWD=Profile[rad_pos.x-2+rad_pos.y*32];
            Line→currnode→rad=rad_pos.x;
            if(Curr.z>0 && FWD.z==0 && FFWD.z==0 &&
                BKWD.z>0        &&        BBKWD.z>0)
                {Line→currnode→fixed=1;}
            else if(Curr.z==0 && FWD.z==0 && FFWD.z==0)
                {Line→currnode→fixed=1;}
            else if(Curr.z==0 && BKWD.z==0 && BBK-
                WD.z==0){Line→currnode→fixed=1;}}
```

APPENDIX B

Volumetric Vessel Flux

```
void Volumetric_Vessel_Track(Vol_Ves_Data*Data)
{const int res_size=32;
    float3 pos=Data→SP;
    int dir=Data→dir;
    int dim_ax=Data→dim;
    Node Tmp;
    int mx_rad=8, mx_dost=8;
    int    hdim_ax=ftoi(dim_ax/2),    dim_z=(ftoi(dim_ax)),
        hdim_z=ftoi(dim_z/2), dmax=dim_ax-1, dmz=dim_z-
        1;
    int3 pos_i, tmp_pos_i, pos_off_i, blk_SP;
    float3 tmp1, curr, sum, next, Osteum=pos;
    int res_cnt=0, alt_cnt=0;
    float d_ost, dist;
    float brk_pts[h_dim*res_size]; float res_array[64*64*6];
    float3 res_pos_array[64*64*6];
//create the data storage structures
    int    cnt_vs0=0,    cnt_vs1=0,    cnt_vs2=0,    cnt_vs3=0,
        cnt_vs4=0, cnt_vs5=0;
    int    vs0_pos=0,    vs1_pos=0,    vs2_pos=0,    vs3_pos=0,
        vs4_pos=0, vs5_pos=0, sum_cnt=1;
    float3   POTENTIAL_VS0[x_dim];   float3   POTEN-
        TIAL_VS1[x_dim]; float3 POTENTIAL_VS2[x_dim];
        float3   POTENTIAL_VS3[x_dim];   float3   POTEN-
        TIAL_VS4[x_dim]; float3 POTENTIAL_VS5[x_dim];
    float3  *tmp_vs0=new  float3[res_size];  float3  *tmp_
        vs1=new float3[res_size]; float3 *tmp_vs2=new float3
        [res_size];
    float3   *tmp_vs3=new   float3[res_size];   float3   *tmp_
        vs4=new float3[res_size]; float3 *tmp_vs5=new float3
        [res_size];
    float *vs0_area=new float[res_size]; float *vs1_area=new
        float[res_size]; float *vs2_area=new float[res_size];
    float *vs3_area=new float[res_size]; float *vs4_area=new
        float[res_size]; float *vs5_area=new float[res_size];
    pos_i=f3toi3(pos); Tmp=Get_Random_i3(pos_i); //float
        vval=Tmp.wall;
    blk_SP.x=0; blk_SP.y=0; blk_SP.z=0;
    if(dir==0){blk_SP.x=hdim_ax-1;        blk_SP.y=0;
        blk_SP.z=hdim_z-1;}
    else if(dir==1){blk_SP.x=hdim_ax-1; blk_SP.y=dim_ax-
        1; blk_SP.z=hdim_z-1;}
    else if(dir==2){blk_SP.x=dim_ax-1; blk_SP.y=hdim_ax-
        1; blk_SP.z=hdim_z-1;}
    else    if(dir==3){blk_SP.x=0;    blk_SP.y=hdim_ax-1;
        blk_SP.z=hdim_z-1;}
    else            if(dir==4){blk_SP.x=hdim_ax-1;
        blk_SP.y=hdim_ax-1; blk_SP.z=dim_z-1;}
    else            if(dir==5){blk_SP.x=hdim_ax-1;
        blk_SP.y=hdim_ax-1; blk_SP.z=0;}
//Comment B//
    for(int i=0;i<dim_ax;i++)
    {for(int j=0;j<dim_ax;j++)
        {for(int k=0;k<dim_z;k++)
        {pos_off_i.x=i-blk_SP.x;
        pos_off_i.y=j-blk_SP.y;
        pos_off_i.z=k-blk_SP.z;
        tmp_pos_i=pos_i;
        tmp_pos_i.x+=pos_off_i.x;
        tmp_pos_i.y+=pos_off_i.y;
        tmp_pos_i.z+=pos_off_i.z;
        Tmp=Get_Random_i3(tmp_pos_i);    //Comment
            C//
        if(i==0||j==0||k==0||i==dim_ax-1||j==dim_ax-
            1||k==dim_z-1)
        {if(Tmp.wall>V_Wall && Tmp.wall<V_WF)
            {res_pos_array[res_cnt].x=tmp_pos_i.x;   res_
            pos_array[res_cnt].y=tmp_pos_i.y; res_pos_ar-
            ray[res_cnt].z=tmp_pos_i.z;    res_array[res_
            cnt]=Tmp.wall; res_cnt++; alt_cnt++;}}{sum }
//Comment D//
    if(dir==0 && res_cnt!=0)
    {for(int j=0;j<res_cnt;j++)
        {tmp1=res_pos_array[j];    d_ost=Distf3(Osteum,
            tmp1);
        if(tmp1.y<=Osteum.y && d_ost<mx_dost){PO-
            TENTIAL_VS1[cnt_vs1]=tmp1; cnt_vs1++;}
        else {
            if(tmp1.y>=Osteum.y+dmax){POTEN-
            TIAL_VS0[cnt_vs0]=tmp1; cnt_vs0++;}
            else if(tmp1.x<=Osteum.x-(hdim_ax-1)){PO-
            TENTIAL_VS2[cnt_vs2]=tmp1; cnt_vs2++;}
            else if(tmp1.x>=Osteum.x+(hdim_ax-1)){PO-
            TENTIAL_VS3[cnt_vs3]=tmp1; cnt_vs3++;}
            else    if(tmp1.z<=Osteum.z-(hdim_z-1)){PO-
            TENTIAL_VS4[cnt_vs4]=tmp1; cnt_vs4++;}
            else    if(tmp1.z>=Osteum.z+(hdim_z-1)){PO-
            TENTIAL_VS5[cnt_vs5]=tmp1; cnt_vs5++;}
        }{sum
    else if(dir==1 && res_cnt!=0)
    {for(int j=0;j<res_cnt;j++)
        {tmp1=res_pos_array[j];    d_ost=Distf3(Osteum,
            tmp1);
        if(tmp1.y>=Osteum.y && d_ost<mx_dost){PO-
            TENTIAL_VS0[cnt_vs0]=tmp1; cnt_vs0++;}
        else {
            if(tmp1.y<=Osteum.y-dmax){POTEN-
            TIAL_VS1[cnt_vs1]=tmp1; cnt_vs1++;}
            else if(tmp1.x<=Osteum.x-(hdim_ax-1)){PO-
            TENTIAL_VS2[cnt_vs2]=tmp1; cnt_vs2++;}
            else if(tmp1.x>=Osteum.x+(hdim_ax-1)){PO-
            TENTIAL_VS3[cnt_vs3]=tmp1; cnt_vs3++;}
            else    if(tmp1.z<=Osteum.z-(hdim_z-1)){PO-
            TENTIAL_VS4[cnt_vs4]=tmp1; cnt_vs4++;}
            else    if(tmp1.z>=Osteum.z+(hdim_z-1)){PO-
            TENTIAL_VS5[cnt_vs5]=tmp1; cnt_vs5++;}
        }{sum
```

```
else if(dir==2 && res_cnt!=0)
  {for(int j=0;j<res_cnt;j++)
    {tmp1=res_pos_array[j];    d_ost=Distf3(Osteum,
      tmp1);
    if(tmp1.x>=Osteum.x && d_ost<mx_dost)
      {POTENTIAL_VS3[cnt_vs3]=tmp1;
      cnt_vs3++;}
    else{
      if(tmp1.x<=Osteum.x-dmax){POTEN-
        TIAL_VS2[cnt_vs2]=tmp1; cnt_vs2++;}
      else if(tmp1.y<=Osteum.y-(hdim_ax-1)){PO-
        TENTIAL_VS1[cnt_vs1]=tmp1; cnt_vs1++;}
      else if(tmp1.y>=Osteum.y+(hdim_ax-1)){PO-
        TENTIAL_VS0[cnt_vs0]=tmp1; cnt_vs0++;}
      else if(tmp1.z<=Osteum.z-(hdim_z-1)){PO-
        TENTIAL_VS4[cnt_vs4]=tmp1; cnt_vs4++;}
      else if(tmp1.z>=Osteum.z+(hdim_z-1)){PO-
        TENTIAL_VS5[cnt_vs5]=tmp1; cnt_vs5++;}
    }{sum
else if(dir==3 && res_cnt!=0)
  {for(int j=0;j<res_cnt;j++)
    {tmp1=res_pos_array[j];    d_ost=Distf3(Osteum,
      tmp1);
    if(tmp1.x<=Osteum.x && d_ost<mx_dost)
      {POTENTIAL_VS2[cnt_vs2]=tmp1;
      cnt_vs2++;}
    else{
      if(tmp1.x>=Osteum.x+dmax){POTEN-
        TIAL_VS3[cnt_vs3]=tmp1; cnt_vs3++;}
      else if(tmp1.y<=Osteum.y-(hdim_ax-1)){PO-
        TENTIAL_VS1[cnt_vs1]=tmp1; cnt_vs1++;}
      else if(tmp1.y>=Osteum.y+(hdim_ax-1)){PO-
        TENTIAL_VS0[cnt_vs0]=tmp1; cnt_vs0++;}
      else if(tmp1.z<=Osteum.z-(hdim_z-1)){PO-
        TENTIAL_VS4[cnt_vs4]=tmp1; cnt_vs4++;}
      else if(tmp1.z>=Osteum.z+(hdim_z-1)){PO-
        TENTIAL_VS5[cnt_vs5]=tmp1; cnt_vs5++;}
    }{sum
else if(dir==4 && res_cnt!=0)
  {for(int j=0;j<res_cnt;j++)
    {tmp1=res_pos_array[j];    d_ost=Distf3(Osteum,
      tmp1);
    if(tmp1.z>=Osteum.z && d_ost<mx_dost)
      {POTENTIAL_VS5[cnt_vs5]=tmp1;
      cnt_vs5++;}
    else{
      if(tmp1.z<=Osteum.z-dmz){POTEN-
        TIAL_VS4[cnt_vs4]=tmp1; cnt_vs4++;}
      else if(tmp1.x<=Osteum.x-(hdim_ax-1)){PO-
        TENTIAL_VS2[cnt_vs2]=tmp1; cnt_vs2++;}
      else if(tmp1.x>=Osteum.x+(hdim_ax-1)){PO-
        TENTIAL_VS3[cnt_vs3]=tmp1; cnt_vs3++;}
      else if(tmp1.y<=Osteum.y-(hdim_ax-1)){PO-
        TENTIAL_VS1[cnt_vs1]=tmp1; cnt_vs1++;}
      else if(tmp1.y>=Osteum.y+(hdim_ax-1)){PO-
        TENTIAL_VS0[cnt_vs0]=tmp1; cnt_vs0++;}
    }{sum
else if(dir==5 && res_cnt!=0)
  {for(int j=0;j<res_cnt;j++)
    {tmp1=res_pos_array[j];    d_ost=Distf3(Osteum,
      tmp1);
    if(tmp1.z<=Osteum.z && d_ost<mx_dost)
      {POTENTIAL_VS4[cnt_vs4]=tmp1;
      cnt_vs4++;}
    else{
      if(tmp1.z>=Osteum.z+dmz){POTEN-
        TIAL_VS5[cnt_vs5]=tmp1; cnt_vs5++;}
      else if(tmp1.x<=Osteum.x-(hdim_ax-1)){PO-
        TENTIAL_VS2[cnt_vs2]=tmp1; cnt_vs2++;}
      else if(tmp1.x>=Osteum.x+(hdim_ax-1)){PO-
        TENTIAL_VS3[cnt_vs3]=tmp1; cnt_vs3++;}
      else if(tmp1.y<=Osteum.y-(hdim_ax-1)){PO-
        TENTIAL_VS1[cnt_vs1]=tmp1; cnt_vs1++;}
      else if(tmp1.y>=Osteum.y+(hdim_ax-1)){PO-
        TENTIAL_VS0[cnt_vs0]=tmp1; cnt_vs0++;}
    }{sum
//Comment E//
  if(cnt_vs0>0){Sort_Point_32(POTENTIAL_VS0,
    cnt_vs0);}
  if(cnt_vs1>0){Sort_Point_32(POTENTIAL_VS1,
    cnt_vs1);}
  if(cnt_vs2>0){Sort_Point_32(POTENTIAL_VS2,
    cnt_vs2);}
  if(cnt_vs3>0){Sort_Point_32(POTENTIAL_VS3,
    cnt_vs3);}
  if(cnt_vs4>0){Sort_Point_32(POTENTIAL_VS4,
    cnt_vs4);}
  if(cnt_vs5>0){Sort_Point_32(POTENTIAL_VS5,
    cnt_vs5);}
//Comment F//
  int min_cnt=1;
  //vessel 0
  for(int  j=0;j<cnt_vs0;j++){curr=POTENTIAL_VS0[j];
    brk_pts[j]=0;       for(int       i=j;i<cnt_vs0;i++)
    {next=POTENTIAL_VS0[i];   dist=Distf3(curr,next);
    if(dist>mx_rad){dist=0;}brk_pts[j]+=dist;}}
  sum.x=0; sum.y=0; sum.z=0;
  for(int   i=0;i<cnt_vs0;i++){sum.x+=POTENTIAL_
    VS0[i].x;  sum.y+=POTENTIAL_VS0[i].y;  sum.z+
    =POTENTIAL_VS0[i].z;
    if(brk_pts[i]==0) {
      if(sum_cnt>=min_cnt)
        {sum.x=sum.x/sum_cnt;  sum.y=sum.y/sum_cnt;
        sum.z=sum.z/sum_cnt;    tmp_vs0[vs0_pos]=
        sum;   vs0_area[vs0_pos]=sum_cnt*2;   sum_
        cnt=1;    sum.x=0;    sum.y=0;    sum.z=0;
        vs0_pos++;}
      else{sum_cnt=1;   sum.x=0;   sum.y=0;   sum.z=0;
        vs0_pos++;}}
    else{sum_cnt++;}}
  //vessel 1
  for(int  j=0;j<cnt_vs1;j++){curr=POTENTIAL_VS1[j];
    brk_pts[j]=0;       for(int       i=j;i<cnt_vs1;i++)
    {next=POTENTIAL_VS1[i];   dist=Distf3(curr,next);
    if(dist>mx_rad){dist=0;}brk_pts[j]+=dist;}}
  sum.x=0; sum.y=0; sum.z=0;
  for(int   i=0;i<cnt_vs1;i++){sum.x+=POTENTIAL_
    VS1[i].x;  sum.y+=POTENTIAL_VS1[i].y;  sum.z+=
    POTENTIAL_VS1[i].z;
    if(brk_pts[i]==0)
      {if(sum_cnt>=min_cnt)
        {sum.x=sum.x/sum_cnt;  sum.y=sum.y/sum_cnt;
        sum.z=sum.z/sum_cnt;   tmp_vs1[vs1_pos]=sum;
        vs1  area[vs1_pos]=sum_cnt*2;   sum_cnt=1;
        sum.x=0; sum.y=0; sum.z=0; vs1_pos++;}
      else{sum_cnt=1;   sum.x=0;   sum.y=0;   sum.z=0;
        vs1_pos++;}}else{sum_cnt++;}}
  //vessel 2
  for(int  j=0;j<cnt_vs2;j++){curr=POTENTIAL_VS2[j];
    brk_pts[j]=0;       for(int       i=j;i<cnt_vs2;i++)
    {next=POTENTIAL_VS2[i];   dist=Distf3(curr,next);
    if(dist>mx_rad){dist=0;}brk_pts[j]+=dist;}}
```

```
sum.x=0; sum.y=0; sum.z=0;
for(int     i=0;i<cnt_vs2;i++){sum.x+=POTENTIAL_
    VS2[i].x;  sum.y+=POTENTIAL_VS2[i].y;  sum.z+=
    POTENTIAL_VS2[i].z;
    if(brk_pts[i]==0)
    {if(sum_cnt>=min_cnt)
        {sum.x=sum.x/sum_cnt;     sum.y=sum.y/sum_cnt;
         sum.z=sum.z/sum_cnt;  tmp_vs2[vs2_pos]=sum;
         vs2_area[vs2_pos]=sum_cnt*2;      sum_cnt=1;
         sum.x=0; sum.y=0; sum.z=0; vs2_pos++;}
        else{sum_cnt=1;  sum.x=0;  sum.y=0;  sum.z=0;
         vs0_pos++;}
    }else{sum_cnt++;}}
//vessel 3
for(int   j=0;j<cnt_vs3;j++){curr=POTENTIAL_VS3[j];
    brk_pts[j]=0;      for(int      i=j;i<cnt_vs3;i++)
    {next=POTENTIAL_VS3[i];  dist=Distf3(curr,next);
    if(dist>mx_rad){dist=0;}brk_pts[j]+=dist;}}
sum.x=0; sum.y=0; sum.z=0;
for(int     i=0;i<cnt_vs3;i++){sum.x+=POTENTIAL_
    VS3[i].x;  sum.y+=POTENTIAL_VS3[i].y;  sum.z+=
    POTENTIAL_VS3[i].z;
    if(brk_pts[i]==0)
    {if(sum_cnt>=min_cnt)
        {sum.x=sum.x/sum_cnt;     sum.y=sum.y/sum_cnt;
         sum.z=sum.z/sum_cnt;  tmp_vs3[vs3_pos]=sum;
         vs3_area[vs3_pos]=sum_cnt*2;      sum_cnt=1;
         sum.x=0; sum.y=0; sum.z=0; vs3_pos++;}
        else{sum_cnt=1;  sum.x=0;  sum.y=0;  sum.z=0;
         vs0_pos++;}
    }else{sum_cnt++;}}
//vessel 4
for(int   j=0;j<cnt_vs4;j++){curr=POTENTIAL_VS4[j];
    brk_pts[j]=0;      for(int      i=j;i<cnt_vs4;i++)
    {next=POTENTIAL_VS4[i];  dist=Distf3(curr,next);
    if(dist>mx_rad){dist=0;}brk_pts[j]+=dist;}}
sum.x=0; sum.y=0; sum.z=0;
for(int     i=0;i<cnt_vs4;i++){sum.x+=POTENTIAL_
    VS4[i].x;  sum.y+=POTENTIAL_VS4[i].y;  sum.z+=
    POTENTIAL_VS4[i].z;
    if(brk_pts[i]==0) {
      if(sum_cnt>=min_cnt){sum.x=sum.x/sum_cnt;
         sum.y=sum.y/sum_cnt;     sum.z=sum.z/sum_cnt;
         tmp_vs4[vs4_pos]=sum;       vs4_area[vs4_pos]=
         sum_cnt;   sum_cnt=1;   sum.x=0;   sum.y=0;
         sum.z=0; vs4_pos++;}
        else{sum_cnt=1;  sum.x=0;  sum.y=0;  sum.z=0;
         vs0_pos++;}
    }else{sum_cnt++;}}
//vessel 5
for(int   j=0;j<cnt_vs5;j++){curr=POTENTIAL_VS5[j];
    brk_pts[j]=0;      for(int      i=j;i<cnt_vs5;i++)
    {next=POTENTIAL_VS5[i];  dist=Distf3(curr,next);
    if(dist>mx_rad){dist=0;}brk_pts[j]+=dist;}}
sum.x=0; sum.y=0; sum.z=0;
for(int     i=0;i<cnt_vs5;i++){sum.x+=POTENTIAL_
    VS5[i].x;  sum.y+=POTENTIAL_VS5[i].y;  sum.z+=
    POTENTIAL_VS5[i].z;
    if(brk_pts[i]==0)
    {if(sum_cnt>=min_cnt){sum.x=sum.x/sum_cnt;
         sum.y=sum.y/sum_cnt;      sum.z=sum.z/sum_cnt;
         tmp_vs5[vs5_pos]=sum; vs5_area[vs5_pos]=sum_
         cnt;   sum_cnt=1;   sum.x=0;   sum.y=0;   sum.z=0;
         vs5_pos++;}
        else{sum_cnt=1;  sum.x=0;  sum.y=0;  sum.z=0;
         vs0_pos++;}
    }else{sum_cnt++;}}
//Comment G//
    if(vs0_pos==0){Data→vs0_pos=0;
        Data→tmp_vs0=NULL;Data→vs0_area=NULL;
        delete[  ]tmp_vs0;   delete[  ]vs0_area;}else{Da-
        ta→vs0_pos=vs0_pos;       Data→tmp_vs0=tmp_vs0;
        Data→vs0_area=vs0_area;}
    if(vs1_pos==0){Data→vs1_pos=0;
        Data→tmp_vs1=NULL;Data→vs1_area=NULL;
        delete[   ]tmp_vs1;   delete[   ]vs1  area;}else{Da-
        ta→vs1_pos=vs1_pos;Data→tmp_vs1=tmp_vs1;
        Data→vs1 area=vs1_area;}
    if(vs2_pos==0){Data→vs2_pos=0;
        Data→tmp_vs2=NULL;Data→vs2_area=NULL;
        delete[   ]tmp_vs2;   delete[   ]vs2_area;}else{Da-
        ta→vs2_pos=vs2_pos;Data→tmp_vs2=tmp_vs2;
        Data→vs2_area=vs2_area;}
    if(vs3_pos==0){Data→vs3_pos=0;
        Data→tmp_vs3=NULL;Data→vs3_area=NULL;
        delete[   ]tmp_vs3;   delete[   ]vs3_area;}else{Da-
        ta→vs3_pos=vs3_pos;       Data→tmp_vs3=tmp_vs3;
        Data→vs3_area=vs3_area;}
    if(vs4_pos==0){Data→vs4_pos=0;
        Data→tmp_vs4=NULL;Data→vs4_area=NULL;
        delete[   ]tmp_vs4;   delete[   ]vs4_area;}else{Da-
        ta→vs4_pos=vs4_pos;Data→tmp_vs4=tmp_vs4;
        Data→vs4_area=vs4_area;}
    if(vs5_pos==0){Data→vs5_pos=0;
        Data→tmp_vs5=NULL;Data→vs5_area=NULL;
        delete[   ]tmp_vs5;   delete[   ]vs5_area;}else{Da-
        ta→vs5_pos=vs5_pos;       Data→tmp_vs5=tmp_vs5;
        Data→vs5_area=vs5_area;}
    Data→tot_pt=vs0_pos+vs1_pos+vs2_pos+vs3_pos+
        vs4_pos+vs5_pos;}
```

What is claimed is:

1. A method comprising:

receiving image data from a scan of a subject, the image data representing first voxels and second voxels;

automatically discerning one or more bones of the subject, based at least in part on the image data;

automatically identifying one or more of the discerned bones;

automatically discerning one or more arteries of the subject, based at least in part on the image data;

automatically identifying one or more of the discerned arteries;

automatically discerning one or more organs of the subject, based at least in part on the image data;

automatically identifying one or more of the discerned organs;

automatically determining a branch point of one of the one or more arteries of the subject; and producing output that depicts one or more of the identified bones, one or more of the identified arteries, or one or more of the identified organs, wherein the branch point of the one of the one or more arteries of the subject is automatically determined by automatic image recognition software executed by a processor, or at least one of the bones, arteries and organs of the subject is automatically discerned or automatically identified by the automatic image recognition software executed by the processor, wherein the automatically discerning the one or more bones, arteries and organs of the subject, the automatically identifying the one or more discerned bones, arteries and organs, and the automatically determining a branch point of one of the one or more arteries of the subject comprise:
  for each of at least some of the first voxels, comparing the respective first voxel with a threshold value of radiodensity and with a radiodensity value of a respective one of the second voxels to produce an array, wherein the respective one of the second voxels is a neighboring voxel of the respective first voxel, and
  using the array, converting the image data to an output image wherein the identified one or more discerned bones, arteries and organs, and the determined branch point of one of the one or more arteries of the subject are identified,
  wherein the array is produced by operations comprising:
    for each of the compared first voxels, based at least in part on the comparison, assigning a respective identifier to the respective compared first voxel, the respective identifier indicating a respective particular one of the identified bones, arteries, or organs, or the determined branch point; and
    for each of the compared first voxels, storing in the array a radiodensity value of the respective compared first voxel, a radiodensity gradient value of the respective compared first voxel, and the respective identifier assigned to the respective compared first voxel, wherein the radiodensity gradient value of the respective compared first voxel indicates a value of radiodensity of the respective compared first voxel relative to radiodensity values of voxels neighboring the respective compared first voxel.

2. The method according to claim 1,
wherein the automatically discerning the one or more bones, arteries and organs of the subject and the automatically identifying the one or more discerned bones, arteries and organs comprise:
performing a reverse wire framing process on the image data.

3. The method according to claim 1, further comprising:
automatically discerning an outer margin of a body wall of the subject;
automatically discerning an inner margin of the body wall of the subject; and
automatically excluding the body wall when discerning at least one of the one or more arteries.

4. The method according to claim 1, further comprising:
automatically detecting a variation from normal anatomy; and
producing output that highlights the detected variation.

5. The method according to claim 1, wherein the operation of automatically discerning one or more bones of the subject comprises:
automatically discerning an outer margin of at least one of the one or more bones; and
automatically classifying medullary bone tissue within the outer margin as part of the at least one of the one or more bones.

6. The method according to claim 1, wherein the operation of receiving image data from a scan of a subject comprises at least one operation from the group consisting of:
receiving image data from a computer tomography (CT) scan of a subject;
receiving image data from a magnetic resonance imaging (MRI) scan of a subject.

7. The method according to claim 1, further comprising:
comparing candidate or discerned points, features or structures of the subject with one or more anatomical models.

8. An article of manufacture comprising:
a non-transitory machine accessible storage medium; and
instructions in the machine accessible storage medium, wherein the instructions, when executed by a machine, enable the machine to perform operations comprising:
  receiving image data from a scan of a subject, the image data representing first voxels and second voxels;
  automatically discerning one or more bones of the subject, based at least in part on the image data;
  automatically identifying one or more of the discerned bones;
  automatically discerning one or more arteries of the subject, based at least in part on the image data;
  automatically identifying one or more of the discerned arteries;
  automatically discerning one or more organs of the subject, based at least in part on the image data;
  automatically identifying one or more of the discerned organs;
  automatically determining a branch point of one of the one or more arteries of the subject; and
  producing output that depicts one or more of the identified bones, one or more of the identified arteries, or one or more of the identified organs,
  wherein the branch point of the one of the one or more arteries of the subject is automatically determined by automatic image recognition software executed by a processor, or at least one of the bones, arteries and organs of the subject is automatically discerned or automatically identified by the automatic image recognition software executed by the processor,
  wherein the automatically discerning the one or more bones, arteries and organs of the subject, the automatically identifying the one or more discerned bones, arteries and organs, and the automatically determining a branch point of one of the one or more arteries of the subject comprise:
    for each of at least some of the first voxels, comparing the respective first voxel with a threshold value of radiodensity and with a radiodensity value of a respective one of the second voxels to produce an array, wherein the respective one of the second voxels is a neighboring voxel of the respective first voxel, and
    using the array, converting the image data to an output image wherein the identified one or more discerned bones, arteries and organs, and the determined branch point of one of the one or more arteries of the subject are identified,
    wherein the array is produced by operations comprising:
      for each of the compared first voxels, based at least in part on the comparison, assigning a respective identifier to the respective compared first voxel, the respective identifier indicating a respective particular one of the identified bones, arteries, or organs, or the determined branch point; and
      for each of the compared first voxels, storing in the array a radiodensity value of the respective compared first voxel, a radiodensity gradient value of the respective compared first voxel, and the respective identifier assigned to the respective compared first voxel, wherein the radiodensity gradient value of the respective compared first voxel indicates a value of radiodensity of the respective compared first voxel relative to radiodensity values of voxels neighboring the respective compared first voxel.

9. The article according to claim 8,
wherein the automatically discerning the one or more bones, arteries and organs of the subject and the automatically identifying the one or more discerned bones, arteries and organs comprise:
performing a reverse wire framing process on the image data.

10. The article according to claim 8, wherein the operations further comprise:
automatically discerning an outer margin of a body wall of the subject;
automatically discerning an inner margin of the body wall of the subject; and
automatically excluding the body wall when discerning at least one of the one or more arteries.

11. The article according to claim 8, wherein the operations further comprise:
automatically detecting a variation from normal anatomy; and
producing output that highlights the detected variation.

12. The article according to claim 8, wherein the operation of automatically discerning one or more bones of the subject comprises:
automatically discerning an outer margin of at least one of the one or more bones; and
automatically classifying medullary bone tissue within the outer margin as part of the at least one of the one or more bones.

13. The article according to claim 8, wherein the operation of receiving image data from a scan of a subject comprises at least one operation from the group consisting of:
receiving image data from a computer tomography (CT) scan of a subject;
receiving image data from a magnetic resonance imaging (MRI) scan of a subject.

14. The article according to claim 8, wherein the operations further comprise:
comparing candidate or discerned points, features or structures of the subject with one or more anatomical models.

15. A system comprising:
at least one processor;
at least one machine accessible storage medium responsive to the processor; and
instructions in the machine accessible storage medium, wherein the instructions, when executed by the at least one processor, enable the processor to perform operations comprising:
receiving image data from a scan of a subject, the image data representing first voxels and second voxels;
automatically discerning one or more bones of the subject, based at least in part on the image data;
automatically identifying one or more of the discerned bones;
automatically discerning one or more arteries of the subject, based at least in part on the image data;
automatically identifying one or more of the discerned arteries;
automatically discerning one or more organs of the subject, based at least in part on the image data;
automatically identifying one or more of the discerned organs;
automatically determining a branch point of one of the one or more arteries of the subject; and
producing output that depicts one or more of the identified bones, one or more of the identified arteries, or one or more of the identified organs,
wherein the branch point of the one of the one or more arteries of the subject is automatically determined by automatic image recognition software executed by the processor, or at least one of the bones, arteries and organs of the subject is automatically discerned or automatically identified by the automatic image recognition software executed by the processor,
wherein the automatically discerning the one or more bones, arteries and organs of the subject, the automatically identifying the one or more discerned bones, arteries and organs, and the automatically determining a branch point of one of the one or more arteries of the subject comprise:
for each of at least some of the first voxels, comparing the respective first voxel with a threshold value of radiodensity and with a radiodensity value of a respective one of the second voxels to produce an array, wherein the respective one of the second voxels is a neighboring voxel of the respective first voxel, and
using the array, converting the image data to an output image wherein the identified one or more discerned bones, arteries and organs, and the determined branch point of one of the one or more arteries of the subject are identified,
wherein the array is produced by operations comprising:
for each of the compared first voxels, based at least in part on the comparison, assigning a respective identifier to the respective compared first voxel, the respective identifier indicating a respective particular one of the identified bones, arteries, or organs, or the determined branch point; and
for each of the compared first voxels, storing in the array a radiodensity value of the respective compared first voxel, a radiodensity gradient value of the respective compared first voxel, and the respective identifier assigned to the respective compared first voxel, wherein the radiodensity gradient value of the respective compared first voxel indicates a value of radiodensity of the respective compared first voxel relative to radiodensity values of voxels neighboring the respective compared first voxel.

16. The system according to claim 15,
wherein the automatically discerning the one or more bones, arteries and organs of the subject and the automatically identifying the one or more discerned bones, arteries and organs comprise:
performing a reverse wire framing process on the image data.

17. The system according to claim 16, wherein the operations further comprise:
automatically discerning an outer margin of a body wall of the subject;
automatically discerning an inner margin of the body wall of the subject; and
automatically excluding the body wall when discerning at least one of the one or more arteries.

18. The system according to claim 15, wherein the operations further comprise:
automatically detecting a variation from normal anatomy; and
producing output that highlights the detected variation.

19. The system according to claim 15, wherein the operation of automatically discerning one or more bones of the subject comprises:
   automatically discerning an outer margin of at least one of the one or more bones; and
   automatically classifying medullary bone tissue within the outer margin as part of the at least one of the one or more bones.

20. The system according to claim 15, wherein the operations further comprise:
   comparing candidate or discerned points, features or structures of the subject with one or more anatomical models.

21. The system according to claim 15, wherein:
   the at least one processor comprises a central processing unit (CPU) and a graphics processing unit (GPU);
   the machine accessible storage medium comprises a system memory responsive to the CPU and a graphics memory responsive to the GPU; and
   the data processing system executes some of the instructions on the CPU and other of the instructions on the GPU.

\* \* \* \* \*